United States Patent
Yomota et al.

(10) Patent No.: US 12,263,004 B2
(45) Date of Patent: Apr. 1, 2025

(54) COGNITIVE FUNCTION DETERMINATION METHOD

(71) Applicants: SHIMADZU CORPORATION, Kyoto (JP); Medical Corporation Sochikai, Tokyo (JP); MCBI INC., Tsukuba (JP)

(72) Inventors: Satoshi Yomota, Kyoto (JP); Shin Nakamura, Kyoto (JP); Eiji Ando, Kyoto (JP); Takashi Asada, Tokyo (JP); Hiroko Nakata, Tsukuba (JP); Kazuhiko Uchida, Tsukuba (JP); Yoshinori Nishimura, Tsukuba (JP)

(73) Assignees: SHIMADZU CORPORATION, Kyoto (JP); Medical Corporation Sochikai, Tokyo (JP); MCBI INC., Tsukuba (JP)

( * ) Notice: Subject to any disclaimer, the term of this patent is extended or adjusted under 35 U.S.C. 154(b) by 505 days.

(21) Appl. No.: 16/628,712

(22) PCT Filed: Jul. 7, 2017

(86) PCT No.: PCT/JP2017/025052
§ 371 (c)(1),
(2) Date: May 11, 2020

(87) PCT Pub. No.: WO2019/008773
PCT Pub. Date: Jan. 10, 2019

(65) Prior Publication Data
US 2020/0268304 A1 Aug. 27, 2020

(51) Int. Cl.
*A61B 5/00* (2006.01)
*A61B 5/026* (2006.01)

(52) U.S. Cl.
CPC .......... *A61B 5/4064* (2013.01); *A61B 5/0261* (2013.01); *A61B 5/483* (2013.01); *A61B 5/4884* (2013.01)

(58) Field of Classification Search
CPC ..... A61B 5/4064; A61B 5/0261; A61B 5/483; A61B 5/4884; A61B 5/0075;
(Continued)

(56) References Cited

U.S. PATENT DOCUMENTS 6,453,193 B1 * 9/2002 Heyrend ................ A61B 5/378
600/544
9,103,013 B2 8/2015 Dorfman et al.
(Continued)

FOREIGN PATENT DOCUMENTS

CN 101584582 A 11/2009
JP 2007-289469 A 11/2007
(Continued)

OTHER PUBLICATIONS

U.S. Appl. No. 62/371,607, filed 2016.*
(Continued)

*Primary Examiner* — Scott M. Getzow
(74) *Attorney, Agent, or Firm* — Sughrue Mion, PLLC

(57) ABSTRACT

A cognitive function determination method includes applying a load including a sensory stimulus (5a) or tasks with different degrees of difficulty a plurality of times (S1), measuring a change in brain activity of a subject (P) when the load is applied and acquiring measurement data (S2), and determining a degree of cognitive function of the subject (P) (S3).

15 Claims, 13 Drawing Sheets

(58) Field of Classification Search
CPC . A61B 2562/0238; A61B 5/168; A61B 10/00; A61B 5/4824; A61B 5/4827; A61B 5/0071; A61B 5/4005
See application file for complete search history.

(56) References Cited

U.S. PATENT DOCUMENTS

| | | | |
|---|---|---|---|
| 9,131,889 | B2 | 9/2015 | Kato et al. |
| 9,886,493 | B2 | 2/2018 | Coleman et al. |
| 10,891,313 | B2 | 1/2021 | Coleman et al. |
| 2004/0167380 | A1* | 8/2004 | Simon ............... A61B 5/16 600/300 |
| 2009/0131995 | A1* | 5/2009 | Sloan ............... A61N 1/0529 607/45 |
| 2014/0275960 | A1* | 9/2014 | Hubbard ............... A61B 5/055 600/410 |
| 2014/0370479 | A1* | 12/2014 | Gazzaley ............... G09B 7/02 434/322 |
| 2015/0080753 | A1 | 3/2015 | Miyazaki et al. |
| 2016/0287160 | A1 | 10/2016 | Sato et al. |
| 2017/0007147 | A1 | 1/2017 | Hasegawa |
| 2018/0078184 | A1 | 3/2018 | Yagi et al. |
| 2018/0125409 | A1 | 5/2018 | Tahara |
| 2018/0228447 | A1 | 8/2018 | Arai et al. |
| 2019/0059799 | A1* | 2/2019 | Arai ............... A61B 5/165 |
| 2019/0159715 | A1* | 5/2019 | Mishra Ramanathan ............... A61B 5/377 |

FOREIGN PATENT DOCUMENTS

| | | |
|---|---|---|
| JP | 2013-518182 A | 5/2013 |
| JP | 2014-133080 A | 7/2014 |
| JP | 2016-189955 A | 11/2016 |
| KR | 10-2015-0076167 A | 7/2015 |
| WO | 2009/099435 A1 | 8/2009 |
| WO | 2012/165602 A1 | 12/2012 |
| WO | 2014052938 A1 | 4/2014 |
| WO | 2015/111331 A1 | 7/2015 |
| WO | 2016/148199 A1 | 9/2016 |
| WO | 2016/195082 A1 | 12/2016 |
| WO | 2017/065318 A1 | 4/2017 |

OTHER PUBLICATIONS

Office Action dated Feb. 11, 2022 from the China National Intellectual Property Administration in CN Application No. 201780094652.8.
Communication issued Jan. 21, 2021 by the Korean Patent Office in application No. 10-2020-7001015.
Kito et al., "Comparison of alterations in cerebral hemoglobin oxygenation in late life depression and Alzheimer's disease as assessed by near-infrared spectroscopy", Behavioral and Brain Functions, BioMed Central, Mar. 2014, 10:8, doi: 10.1186/1744-9081-10-8 (9 pages total).
Notice of Reasons for Refusal dated Aug. 18, 2020 from the Japanese Patent Office in Application No. 2019-528330.
Kazuki Yanagisawa et al., "Measurement and Evaluation of Higher Brain Function Using Functional Near-Infrared Spectroscopy (fNIRS)", The Transaction of Human Interface Society, 2009, pp. 183-191, vol. 11, No. 2.
International Search Report of PCT/JP2017/025052 dated Aug. 15, 2017 [PCT/ISA/210].
Written Opinion of PCT/JP2017/025052 dated Aug. 15, 2017 [PCT/ISA/237].
Office Action dated Oct. 10, 2022 from the China National Intellectual Property Administration in CN Application No. 201780094652.8.

* cited by examiner

FIRST EMBODIMENT

FIRST EMBODIMENT

FIRST EMBODIMENT

FIRST EMBODIMENT

FIRST EMBODIMENT

FIRST EMBODIMENT

FIRST EXAMPLE
Fig. 7 (A) ANALYSIS RESULTS OF NDCS (22 PERSONS)
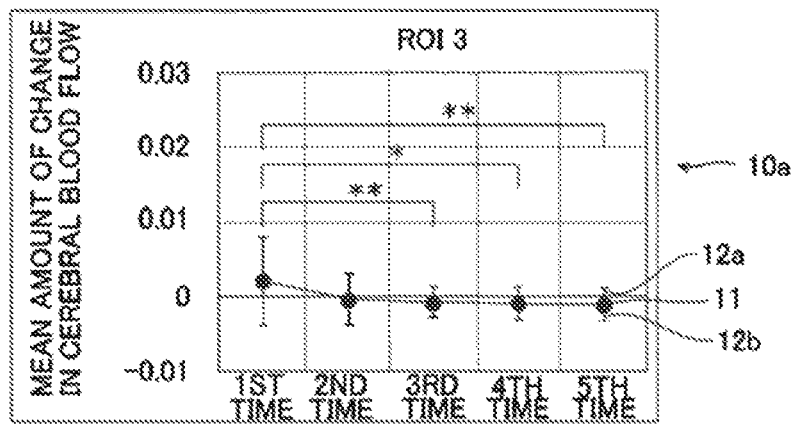
Fig. 7 (B) ANALYSIS RESULTS OF MCIS (27 PERSONS)
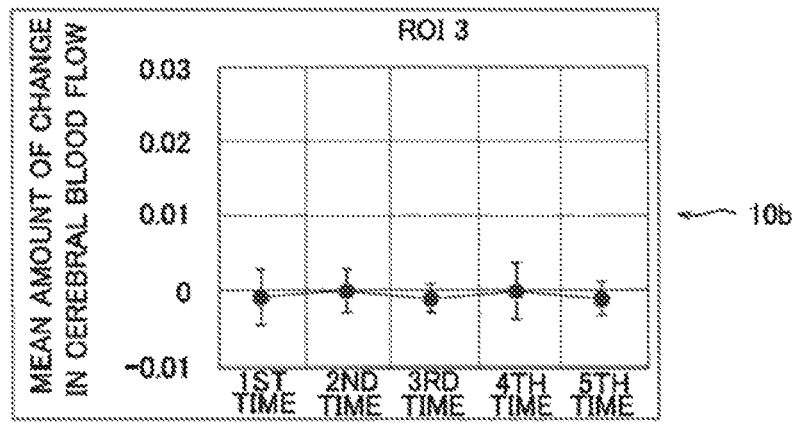
Fig. 7 (C) ANALYSIS RESULTS OF ADS (22 PERSONS)
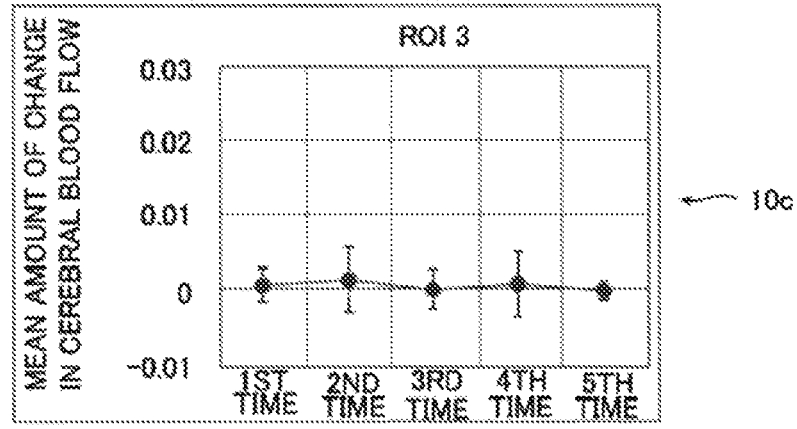

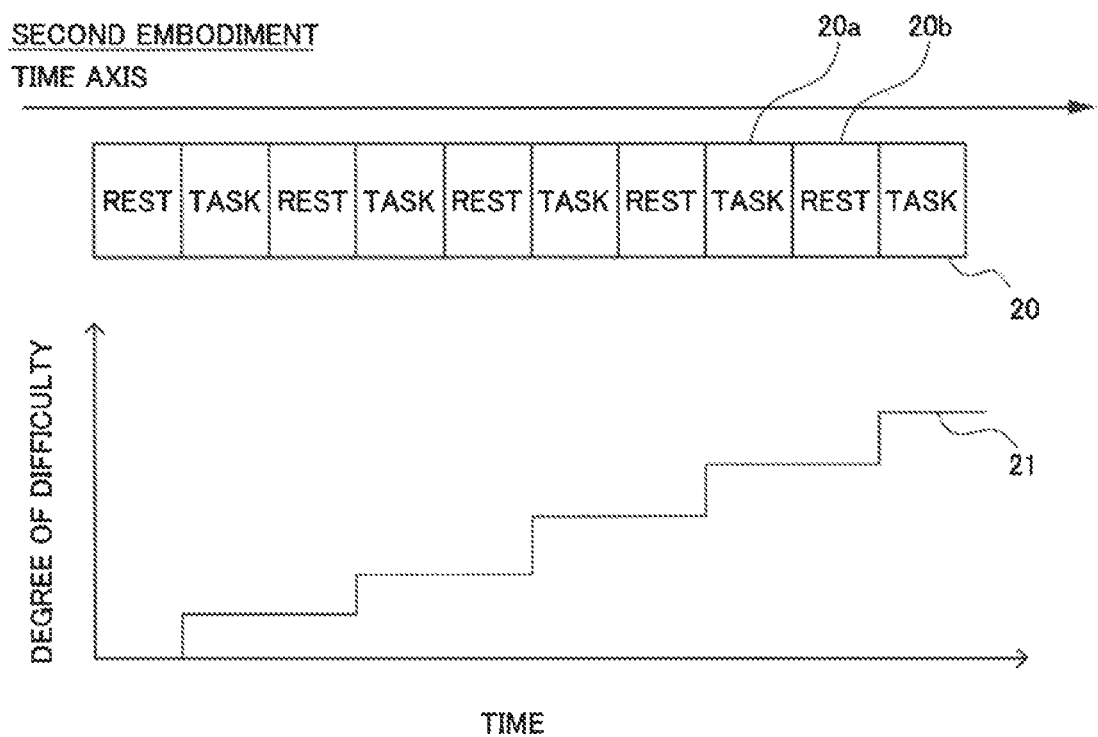

SECOND EXAMPLE
Fig. 9 (A) ANALYSIS RESULTS OF NDCS (22 PERSONS)
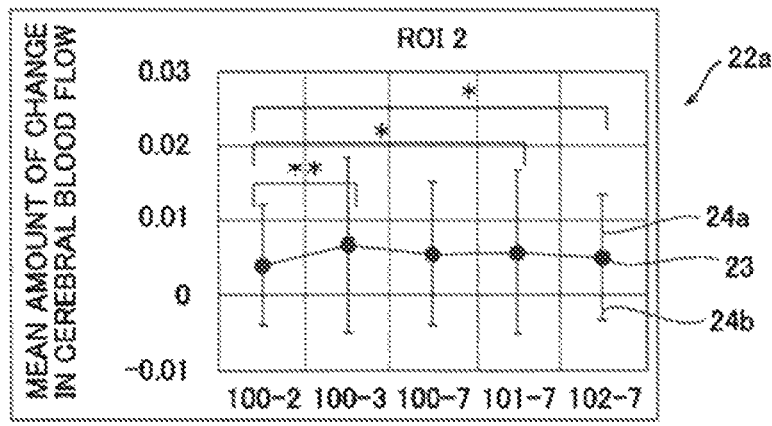
Fig. 9 (B) ANALYSIS RESULTS OF MCIS (27 PERSONS)
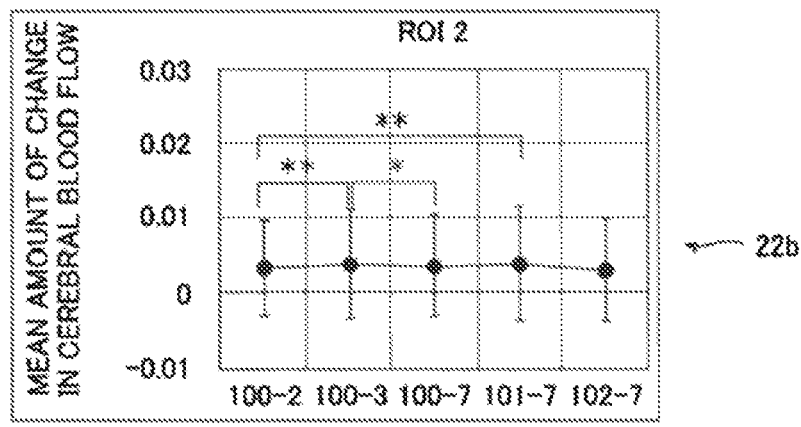
Fig. 9 (C) ANALYSIS RESULTS OF ADS (22 PERSONS)
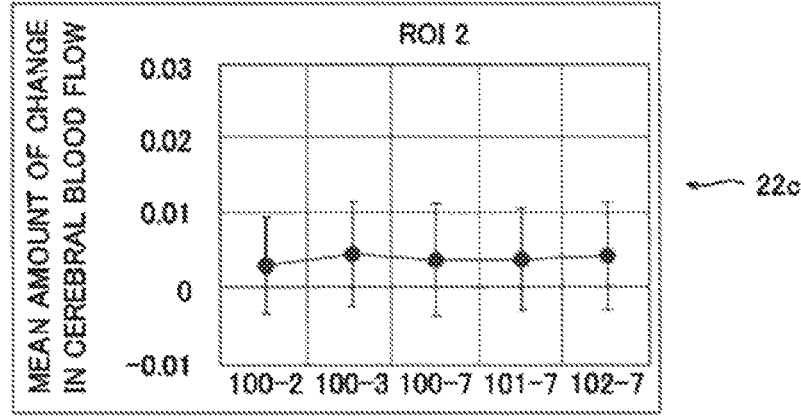

THIRD EMBODIMENT

THIRD EMBODIMENT

FIG.13
THIRD EXAMPLE
Fig. 13 (A) ANALYSIS RESULTS OF CH 10
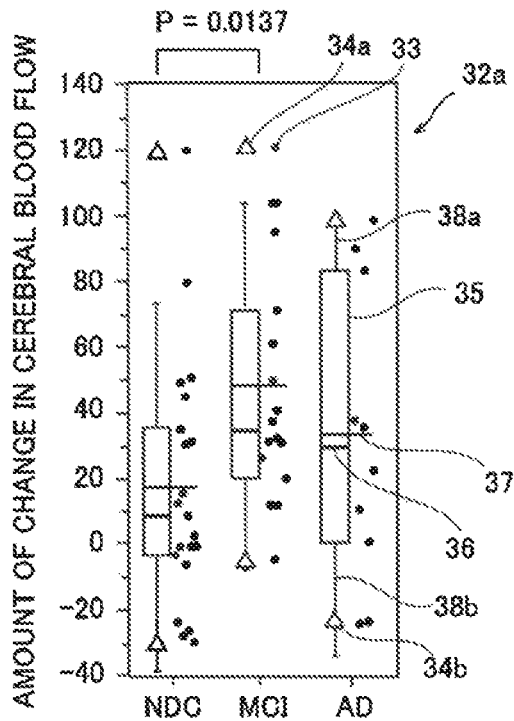
Fig. 13 (B) ANALYSIS RESULTS OF CH 37
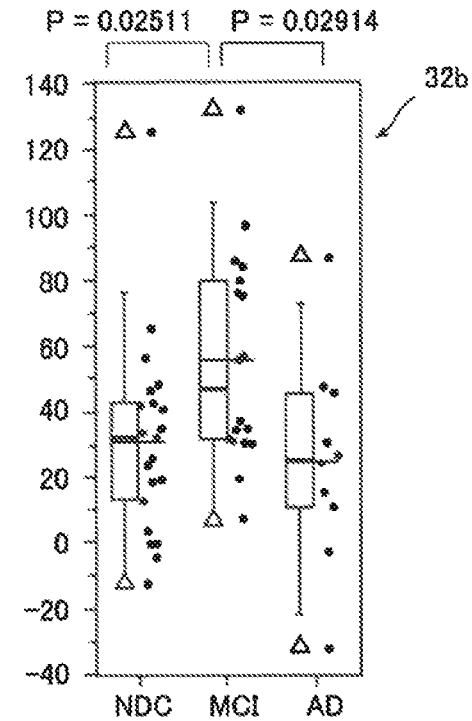
Fig. 13 (C) ANALYSIS RESULTS OF CH 45
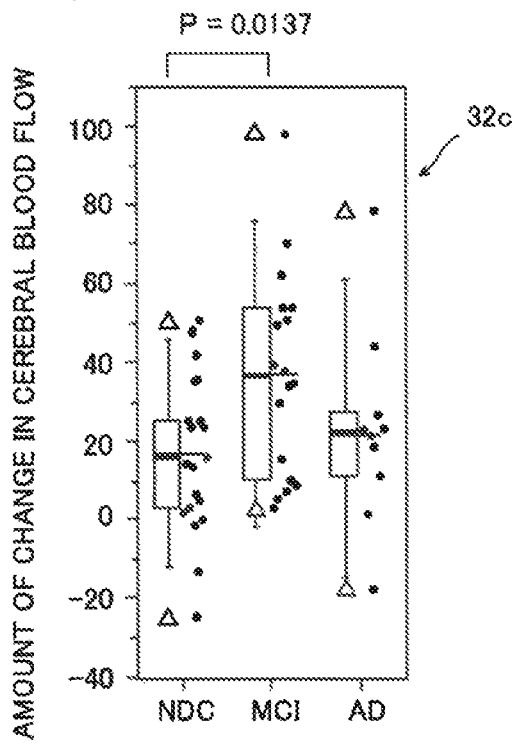
Fig. 13 (D) ANALYSIS RESULTS OF CH 53
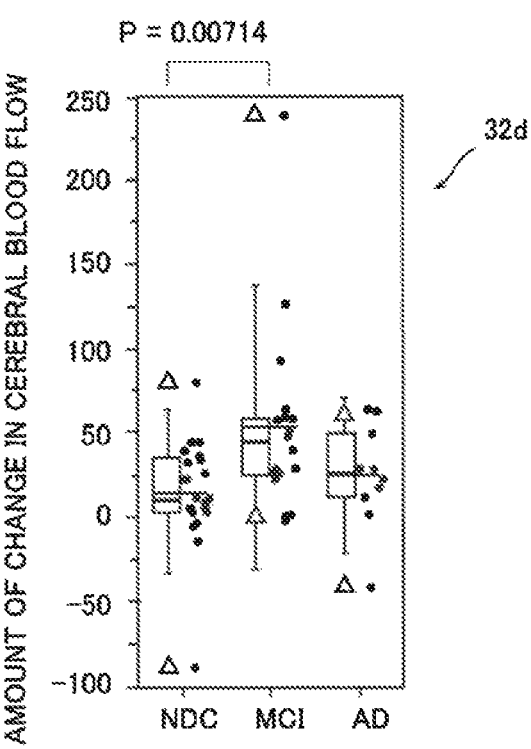

FOURTH EMBODIMENT

FOURTH EMBODIMENT

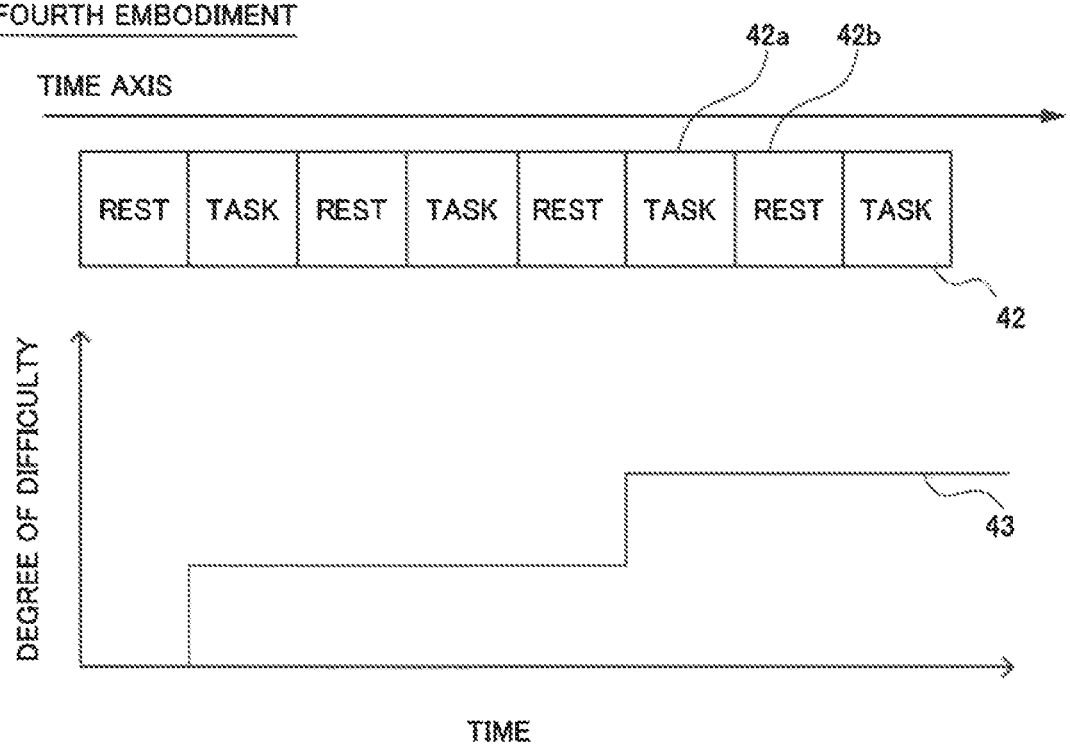

FOURTH EXAMPLE
Fig. 17 (A) ANALYSIS RESULTS OF CH 2
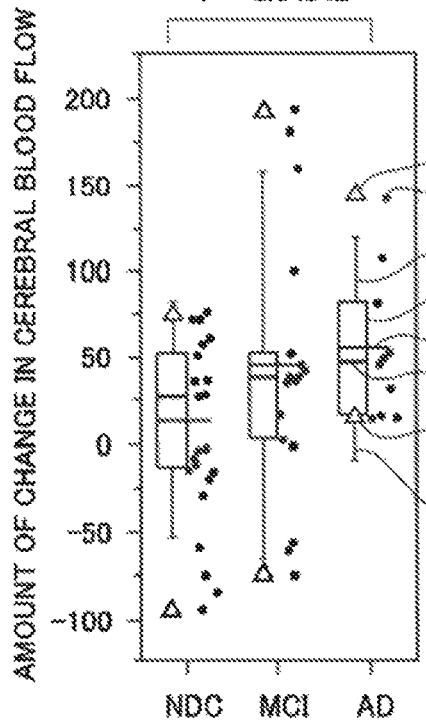
Fig. 17(B) ANALYSIS RESULTS OF CH 32
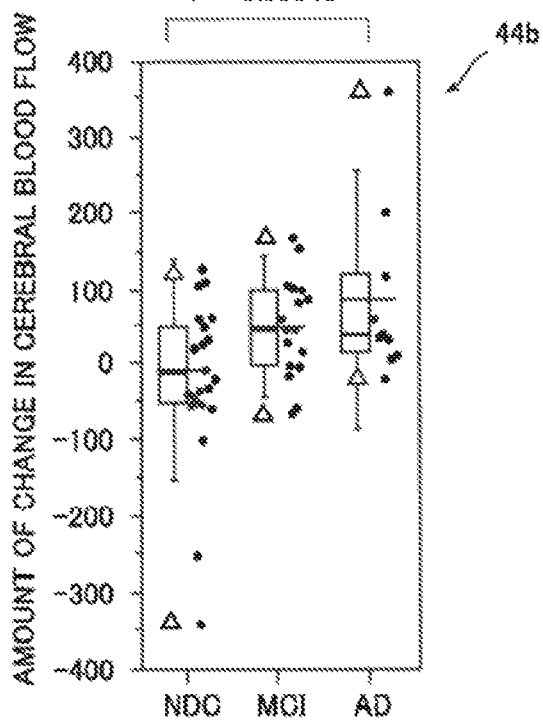
Fig. 17(C) ANALYSIS RESULTS OF CH 52
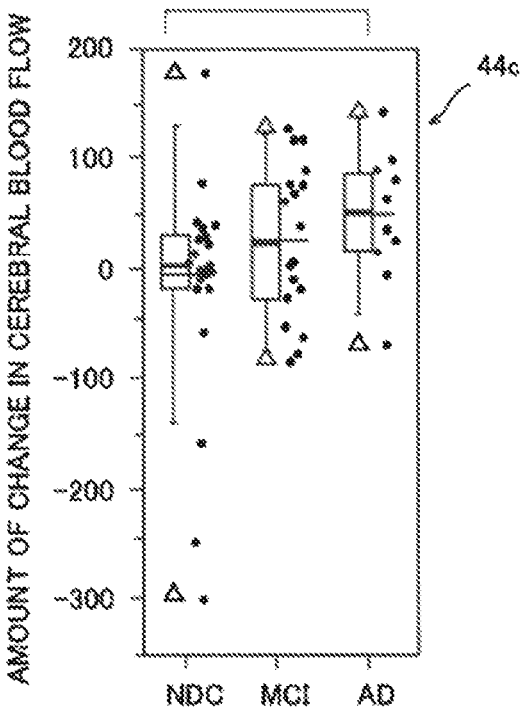

FIFTH EMBODIMENT

COGNITIVE FUNCTION DETERMINATION METHOD

TECHNICAL FIELD

The present invention relates to a cognitive function determination method, and more particularly, it relates to a cognitive function determination method for determining the degree of cognitive function by measuring a change in brain activity.

BACKGROUND ART

Conventionally, a cognitive function determination method for determining the degree of cognitive function by measuring a change in brain activity is known. Such a cognitive function determination method is disclosed in International Publication No. 2012/165602, for example.

International Publication No. 2012/165602 discloses a cognitive impairment determination system that measures cerebral blood flow data during a cognitive task using near-infrared spectroscopy. The cognitive impairment determination system extracts a feature amount from the measured cerebral blood flow data, and determines the subject's cognitive function, using the extracted feature amount and a previously-constructed model used to determine cognitive impairment.

PRIOR ART

Patent Document

Patent Document 1: International Publication No. 2012/165602

SUMMARY OF THE INVENTION

Problem to be Solved by the Invention

The cognitive impairment determination system disclosed in International Publication No. 2012/165602 uses a plurality of types of cognitive tasks when measuring cerebral blood flow data of a subject, but it is believed that tasks with different degrees of difficulty are not given a plurality of times for the same task when the task is given. However, the cerebral blood flow data measured during the cognitive tasks is biased due to familiarity with the task, experience, a level of education, etc. for each subject. Therefore, cognitive tasks with a common and constant degree of difficulty are too easy for some subjects, and thus the brain activity thereof is not detected, and the cognitive tasks with a common and constant degree of difficulty are too difficult for some subjects, and thus they give up executing the tasks.

The present invention is intended to solve the above problem. The present invention aims to provide a cognitive function determination method by which the degree of cognitive function can be determined even when there is an individual difference in subject's adaptation to a cognitive task.

Means for Solving the Problem

In order to attain the aforementioned object, a cognitive function determination method according to an aspect of the present invention includes applying a load including a sensory stimulus to a sensory body of a subject a plurality of times, or applying a load including tasks with different degrees of difficulty to the subject a plurality of times, measuring a change in brain activity of the subject when the load is applied in the applying the load the plurality of times, and acquiring measurement data, and determining a degree of cognitive function of the subject based on an amount of change in the measurement data.

As described above, the method for determining the cognitive function according to this aspect of the present invention includes applying the load including the sensory stimulus to the sensory body of the subject the plurality of times, or applying the load including the tasks with the different degrees of difficulty to the subject the plurality of times, measuring the change in the brain activity of the subject and acquiring the measurement data, and determining the degree of the cognitive function of the subject. Accordingly, when the load including the sensory stimulus is applied to the sensory body of the subject the plurality of times, the change in brain activity can be measured due to the sensory stimulus that does not require understanding of a cognitive task without depending on an individual difference in adaptation to the cognitive task. When the load including the tasks with the different degrees of difficulty is applied to the subject the plurality of times, the change in brain activity due to the task with a degree of difficulty according to the subject can be measured. Consequently, the degree of the cognitive function can be determined even when there is an individual difference in subject's adaptation to the cognitive task.

In aforementioned the cognitive function determination method according to this aspect, the tasks with the different degrees of difficulty are preferably tasks related to at least one of calculation, a combination of memory and imagination, and spatial recognition, and the cognitive function determination method preferably further includes giving each of a plurality of types of sensory stimuli or each of a plurality of types of the tasks with the different degrees of difficulty to the subject the plurality of times, measuring the change in the brain activity of the subject when the sensory stimuli or the tasks are each given in the giving each of the plurality of types of the sensory stimuli or each of the plurality of types of the tasks the plurality of times, and acquiring the measurement data of each of the plurality of types of the sensory stimuli or each of the plurality of types of the tasks, and determining the degree of the cognitive function of the subject based on a result obtained by combining the amount of change in the measurement data of each of the plurality of types of the sensory stimuli or each of the plurality of types of the tasks acquired when each of the plurality of types of the sensory stimuli or each of the plurality of types of the tasks with the different degrees of difficulty is given. Accordingly, the cognitive function can be determined in a complex manner based on the result obtained by combining the data measured from multiple viewpoints. Consequently, the accuracy of determining the degree of the cognitive function of the subject can be improved.

In the aforementioned cognitive function determination method according to this aspect, when the sensory stimulus is applied the plurality of times, a plurality of sensory stimuli having at least two levels of intensity are preferably applied to the subject. Accordingly, the degree of the cognitive function can be determined based on a relative change in the brain activity of the subject with respect to stimuli having different intensities.

In this case, the intensity of the sensory stimulus to be applied to the subject is preferably increased each time the stimulus is applied. Accordingly, the intensity of the stimulus increases as the number of times the stimulus is applied to the subject increases, and thus the degree of the cognitive function can be determined based on a relative change in the brain activity of the subject with respect to the stimulus intensity.

In the aforementioned cognitive function determination method according to this aspect, when the sensory stimulus is applied the plurality of times, the sensory stimulus to be applied to the subject is preferably a persistent stimulus. Accordingly, as the number of times the stimulus is applied to the subject increases, the influence of the stimulus is accumulated (remains), and thus the relative intensity of the stimulus can be gradually increased. Consequently, the degree of the cognitive function can be determined based on a relative change in the brain activity of the subject with respect to the stimulus accumulated as the number of times the stimulus is applied increases. In this specification, the persistent stimulus refers to a stimulus in which the sensation of receiving the stimulus remains even after the stimulus is applied and gradually weakens as time elapses.

In this case, the persistent stimulus is preferably a stimulus given persistence by applying the sensory stimulus while an influence of a previous stimulus remains when the sensory stimulus is applied to the subject. Accordingly, it is easy to gradually increase the relative intensity of the sensory stimulus. Even when there is an individual difference in sensitivity to the sensory stimulus, the response to the intensity change of the sensory stimulus can be measured.

In the aforementioned cognitive function determination method in which the persistent stimulus is given to the subject, the persistent stimulus is preferably a cold stimulus. Accordingly, in comparison with a warm stimulus, for example, a stimulus can be applied to the subject using a cold stimulus having more receptors for the stimulus. Consequently, a change in more active brain activity can be measured.

In the aforementioned cognitive function determination method according to this aspect, the sensory body is preferably a hand of the subject, and the sensory stimulus is preferably a contact stimulus. Accordingly, the stimulus can be applied by directly touching the hand with high sensitivity to the stimulus. Consequently, a more accurate change in brain activity can be measured.

In the aforementioned cognitive function determination method according to this aspect, when the tasks with the different degrees of difficulty are given the plurality of times, the degrees of difficulty of the tasks are preferably set such that a degree of difficulty of a second task given after a first task is higher than a degree of difficulty of the first task. Accordingly, the subject can be accustomed to the tasks using the task with a low degree of difficulty. Consequently, the possibility that the subject gives up executing the tasks halfway can be significantly reduced or prevented. In addition, the tasks with different degrees of difficulty are given a plurality of times such that the subject can be made to execute a task with a degree of difficulty suitable for the subject, and thus failure to detect brain activity can be significantly reduced or prevented.

In the aforementioned cognitive function determination method according to this aspect, the giving the tasks with the different degrees of difficulty the plurality of times preferably includes repeatedly presenting, to the subject, tasks related to calculation with different degrees of difficulty. Accordingly, the possibility that the subject memorizes an answer to a calculation problem due to repeating the same problem can be significantly reduced or prevented. In addition, the subject can be accustomed to the tasks by performing the tasks related to calculation with the different degrees of difficulty the plurality of times, and thus the possibility that the subject stops the tasks halfway can be significantly reduced or prevented. Furthermore, the subject can be made to execute a task with a degree of difficulty suitable for the subject by performing the tasks related to calculation with the different degrees of difficulty the plurality of times. Consequently, the degree of cognitive function related to calculation can be obtained as an index for determining the degree of the cognitive function of the subject, and thus the accuracy of determining the degree of the cognitive function can be improved.

In the aforementioned cognitive function determination method according to this aspect, the giving the tasks with the different degrees of difficulty the plurality of times preferably includes repeatedly presenting, to the subject, tasks in combination of memory with imagination with different degrees of difficulty. Accordingly, the subject can be accustomed to the tasks by performing the tasks in combination of memory with imagination with the different degrees of difficulty the plurality of times, and thus the possibility that the subject stops the tasks halfway can be significantly reduced or prevented. Furthermore, the subject can be made to execute a task with a degree of difficulty suitable for the subject by performing the tasks related to memory and imagination with the different degrees of difficulty the plurality of times. Consequently, the degree of cognitive function related to memory and imagination can be obtained as the index for determining the degree of the cognitive function of the subject, and thus the accuracy of determining the degree of the cognitive function can be improved.

In the aforementioned cognitive function determination method according to this aspect, the giving the tasks with the different degrees of difficulty the plurality of times preferably includes repeatedly presenting, to the subject, tasks related to spatial recognition with different degrees of difficulty. Accordingly, the subject can be accustomed to the tasks by performing the tasks related to spatial recognition with the different degrees of difficulty the plurality of times, and thus the possibility that the subject stops the tasks halfway can be significantly reduced or prevented. Furthermore, the subject can be made to execute a task with a degree of difficulty suitable for the subject by performing the tasks related to spatial recognition with the different degrees of difficulty the plurality of times. Consequently, the degree of cognitive function related to spatial recognition can be obtained as the index for determining the degree of the cognitive function of the subject, and thus the accuracy of determining the degree of the cognitive function can be improved.

In the aforementioned cognitive function determination method according to this aspect, in the acquiring the measurement data, a measurement site is preferably set within a range including any of F3, F4, P3, and P4 in accordance with International 10-20 system. Accordingly, the measurement site for measuring the brain activity can be made substantially constant. Consequently, the occurrence of errors in the measurement data due to different measurement sites can be significantly reduced or prevented. Furthermore, as a result of a test, described below, by the inventors, a significant change in brain activity with respect to the load has been confirmed in any of F3, F4, P3, and P4. Therefore, the degree of the cognitive function can be determined with a significant degree of accuracy.

In the aforementioned cognitive function determination method according to this aspect, the acquiring the measurement data preferably includes measuring a change in cerebral blood flow of the subject as the change in the brain activity by near-infrared spectroscopy (NIRS). Accordingly, a change in the brain activity of the subject can be measured by a NIRS device. Consequently, the NIRS device is non-invasive, and does not require large-scale equipment as compared with magnetic resonance imaging (MRI), for example, and thus a change in the brain activity of the subject can be easily measured. The NIRS device is a device that is attached to the head of the subject and measures a change in brain activity by measuring a change in oxygenated hemoglobin content in the cerebral blood vessel of the subject.

Effect of the Invention

According to the present invention, as described above, it is possible to provide the cognitive function determination method by which the degree of the cognitive function can be determined even when there is an individual difference in subject's adaptation to the cognitive task.

BRIEF DESCRIPTION OF THE DRAWINGS

FIGS. 7(A) to 7(C) are schematic views of statistical results of changes in the brain activity of a non-demented person, a person with mild cognitive impairment, and an Alzheimer's patient according to a first example of the present invention, respectively.

FIG. 8 is a timing chart of a task and a rest, and a graph showing a temporal change in the degree of difficulty of the task according to a second embodiment of the present invention.

FIGS. 9(A) to 9(C) are schematic views of statistical results of changes in the brain activity of a non-demented person, a person with mild cognitive impairment, and an Alzheimer's patient according to a second example of the present invention, respectively.

FIGS. 13(A) to 13(D) are schematic views of statistical results of a channel 10, a channel 37, a channel 45, and a channel 53 in which a significant difference has been observed in changes in brain activity according to a third example of the present invention, respectively.

FIG. 16 is a timing chart of a task and a rest, and a graph showing a temporal change in the degree of difficulty of the task according to the fourth embodiment of the present invention.

FIGS. 17(A) to 17(C) are schematic views of statistical results of a channel 2, a channel 32, and a channel 52 between which a significant difference has been observed in changes in brain activity according to a fourth example of the present invention, respectively.

MODES FOR CARRYING OUT THE INVENTION

Embodiments embodying the present invention are hereinafter described on the basis of the drawings.

First Embodiment

The overall configuration of a brain activity measurement system 100 for implementing a cognitive function determination method according to a first embodiment of the present invention is now described with reference to FIGS. 1 to 3.
(Configuration of Brain Activity Measurement System)

Figure 1:
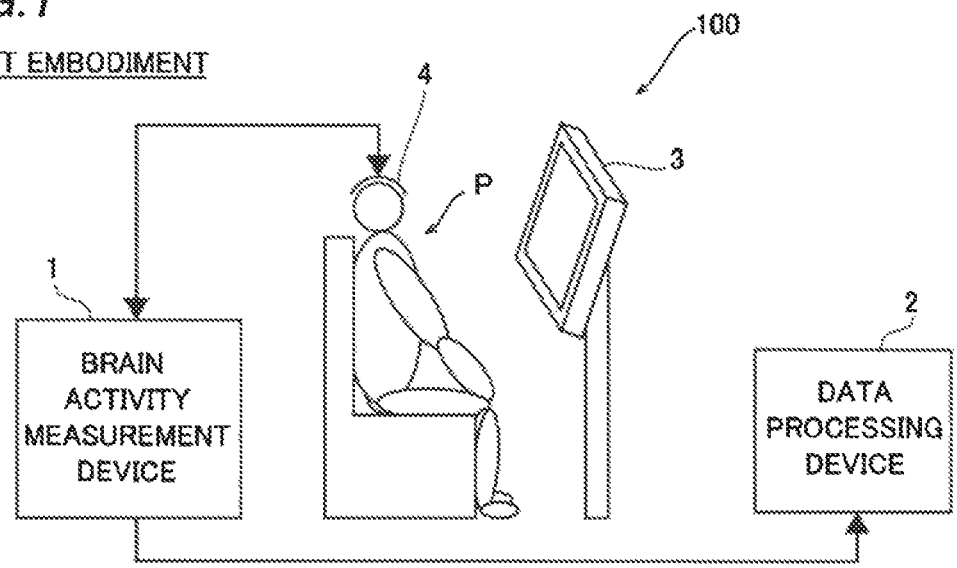
FIG. 1 is a schematic view showing the overall configuration of a brain activity measurement system for implementing a cognitive function determination method according to a first embodiment of the present invention.

As shown in FIG. 1, the brain activity measurement system 100 for implementing the cognitive function determination method according to the first embodiment includes a brain activity measurement device 1, a data processing device 2, and a display device 3.

The brain activity measurement device 1 is a device (optical measurement device) that optically measures the brain activity of a subject P using near-infrared spectroscopy (NIRS) and generates time-series measurement result data. Specifically, the brain activity measurement device 1 is a NIRS device. The brain activity measurement device 1 emits measurement light in a near-infrared wavelength region from light transmitting probes (not shown) arranged on a surface of the head of the subject P. The brain activity measurement device 1 detects the measurement light reflected in the head by causing the measurement light reflected in the head to enter light receiving probes (not shown) arranged on the surface of the head, and acquires the intensity of the measurement light (the amount of received light). A plurality of light transmitting probes and a plurality of light receiving probes are provided, and are attached to a holder 4 configured to fix each probe at a predetermined position on the surface of the head. The brain activity measurement device 1 measures the amount of change in oxygenated hemoglobin, the amount of change in deoxygenated hemoglobin, and the amount of change in total hemoglobin based on the intensity of the measurement light (the amount of received light) at a plurality of wavelengths (three wavelengths of 780 nm, 805 nm, and 830 nm, for example) and the absorption characteristics of hemoglobin.

Thus, the brain activity measurement device 1 measures a cerebral blood flow change according to the brain activity as a change in a hemoglobin amount.

The device configurations of the data processing device 2 and the display device 3 are now described.

The data processing device 2 performs a statistical process of measurement data sent from the brain activity measurement device 1. That is, the data processing device 2 is configured to calculate statistical data for determining the degree of the cognitive function of the subject P. The data processing device 2 includes a personal computer (PC) including a CPU, a memory, a hard disk drive, etc.

The display device 3 is configured to display a task to be executed by the subject P. The display device 3 is a monitor such as a liquid crystal display.

Figure 2:
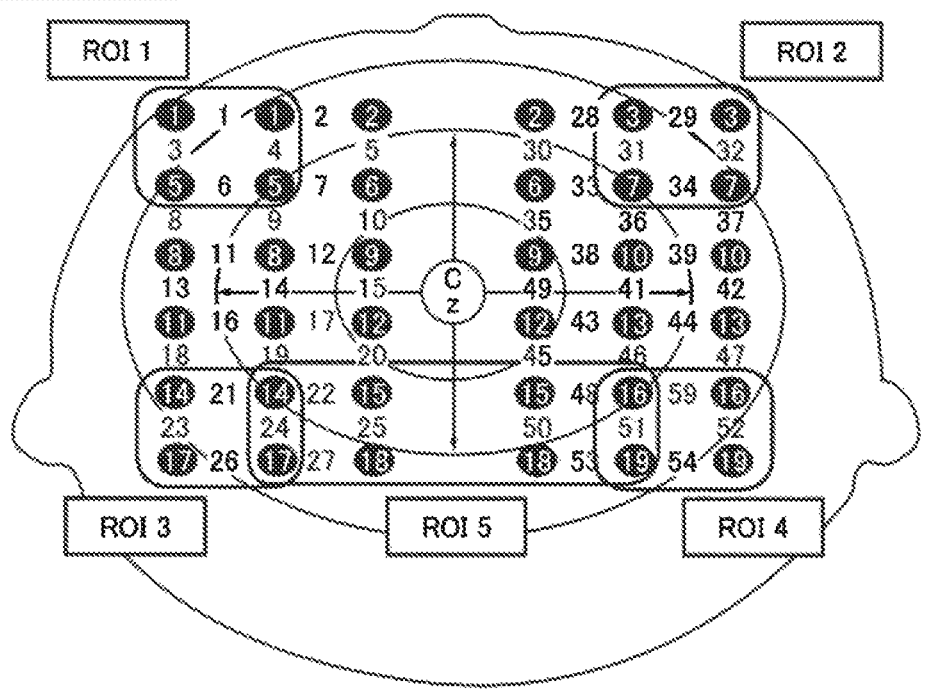
FIG. 2 is a schematic view showing measurement sites for measuring brain activity according to the first embodiment of the present invention.
Figure 3:
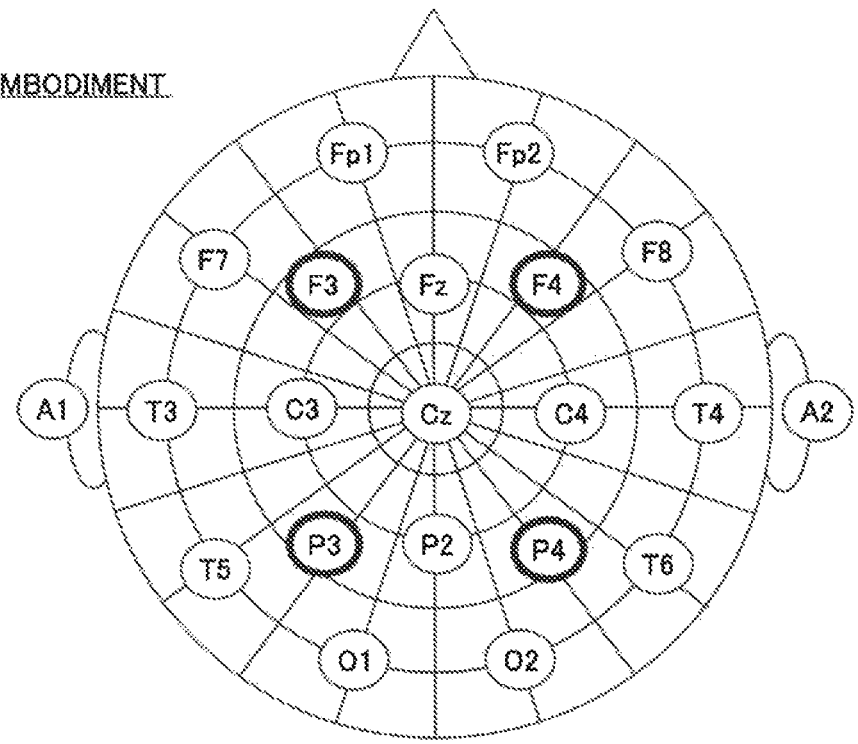
FIG. 3 is a schematic view for illustrating measurement sites in accordance with the International 10-20 system.

FIG. 2 shows measurement sites for measuring the cerebral blood flow of the subject P by the brain activity measurement device 1 in the first embodiment. FIG. 3 is a diagram showing measurement sites in accordance with the International 10-20 system. In the first embodiment, the measurement sites for acquiring the measurement data of the brain activity of the subject P are set within a range including any of F3, F4, P3, and P4 in accordance with the International 10-20 system shown in FIG. 3. Specifically, the measurement sites are set in fifty-four channels as shown in FIG. 2, including any of F3, F4, P3, and P4 in accordance with the International 10-20 system. At this time, ROIs 1 to 15 are set as regions of interest (ROIs).

(Method for Determining Degree of Cognitive Function of Subject)

A method for determining the cognitive function of the subject P according to the first embodiment is now described with reference to FIGS. 1 and 4 to 6.

Figure 4:
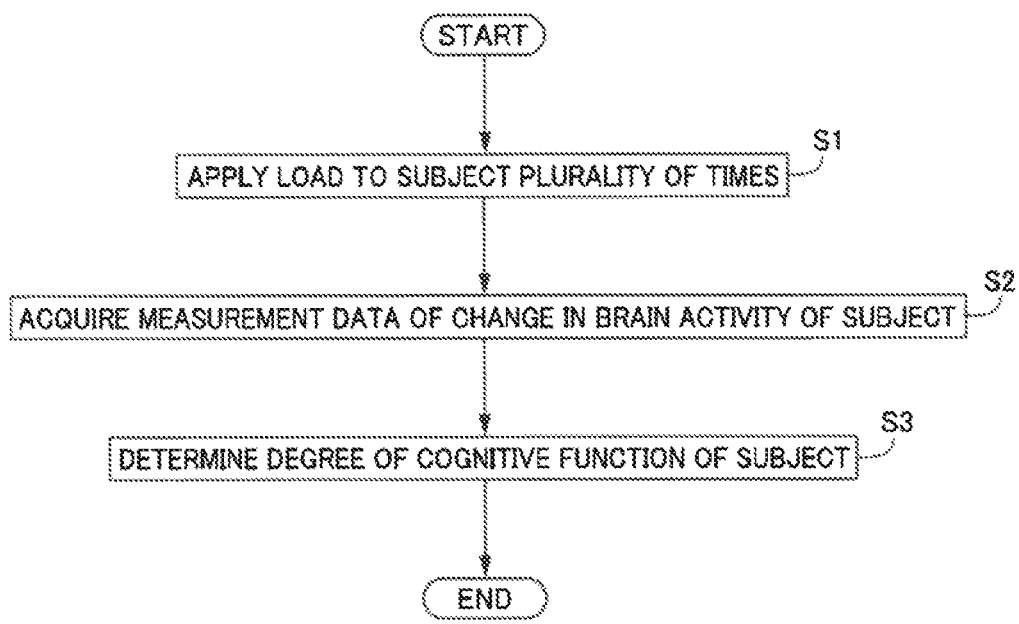
FIG. 4 is a flowchart showing a flow of determining the degree of subject's cognitive function according to the first embodiment of the present invention.

First, the outline of the method for determining the degree of the cognitive function of the subject P is described. FIG. 4 is a flowchart showing a flow of determining the degree of the cognitive function of the subject P. In the first embodiment, the method for determining the degree of the cognitive function of the subject P includes step S1 of applying a load including a sensory stimulus to the sensory body of the subject P a plurality of times, or applying a load including tasks with different degrees of difficulty to the subject P a plurality of times. In addition, the method for determining the degree of the cognitive function of the subject P includes step S2 of measuring a change in the brain activity of the subject P when the load is applied in the step of applying the load a plurality of times, and acquiring measurement data. Furthermore, the method for determining the degree of the cognitive function of the subject P includes step S3 of determining the degree of the cognitive function of the subject P based on the amount of change in the measurement data. Through these steps, the degree of the cognitive function of the subject P is determined.

(Step of Applying Load Including Sensory Stimulus to Sensory Body of Subject Plurality of Times)

The step of applying the load including the sensory stimulus to the sensory body of the subject P a plurality of times is now described with reference to FIGS. 5 and 6.

In the first embodiment, step S1 of applying the load to the subject P a plurality of times is a step of applying a load including a sensory stimulus to the sensory body of the subject P a plurality of times.

Figure 5:
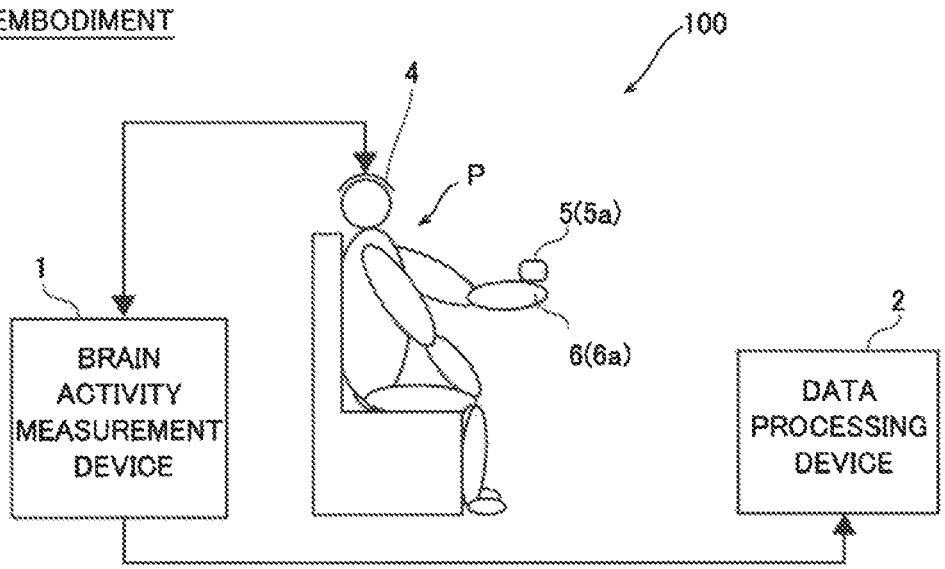
FIG. 5 is a schematic view for illustrating a method for applying a cold stimulus to a subject according to the first embodiment of the present invention.

FIG. 5 is a schematic view at the time of applying a sensory stimulus to the sensory body of the subject P. In an example shown in FIG. 5, a cold stimulus is applied to the subject P by applying an ice pack 5 to the left palm 6a of the subject P. That is, in the first embodiment, the sensory body is the hand 6 of the subject P, and the sensory stimulus is a contact stimulus.

In the first embodiment, the sensory stimulus to be applied to the subject P is a persistent stimulus. The persistent stimulus is a stimulus given persistence by applying a sensory stimulus while the influence of the previous stimulus remains when the sensory stimulus is applied to the subject P. In the first embodiment, the persistent stimulus is a cold stimulus. Something that applies a cold stimulus is the ice pack 5, for example. The ice pack 5 is cooled to 4° C., for example. That is, a cool stimulus having a constant intensity equivalent to 4° C. is applied as the sensory stimulus to the subject P a plurality of times.

Figure 6:
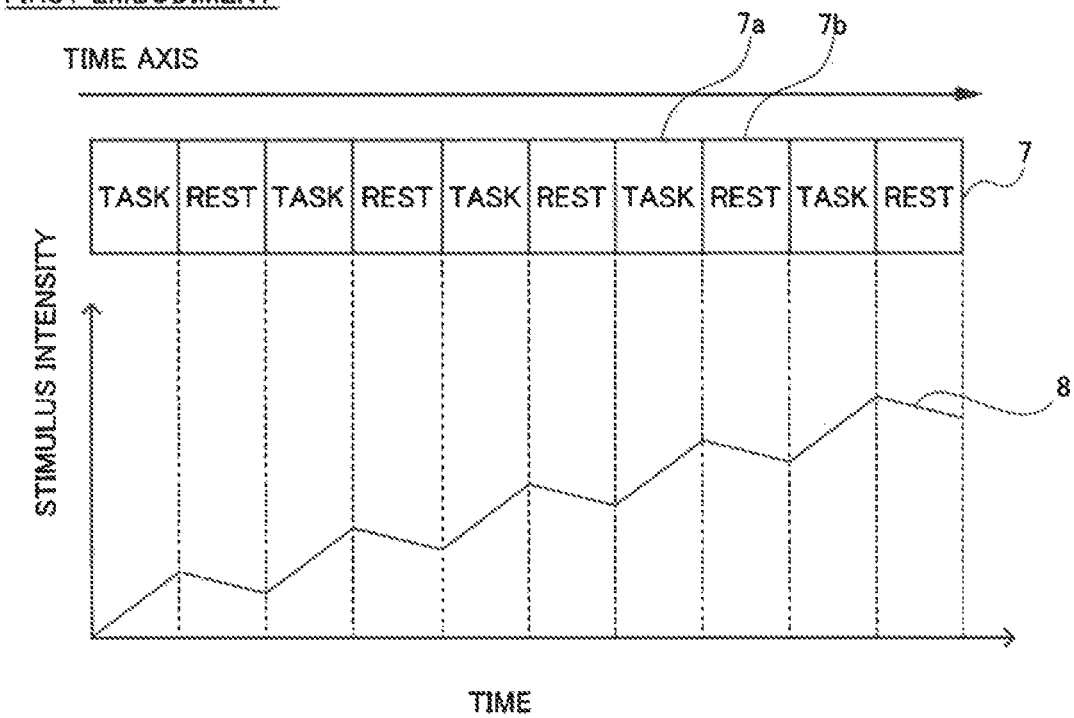
FIG. 6 is a timing chart of a task and a rest, and a graph showing a temporal change in the intensity of the cold stimulus according to the first embodiment of the present invention.

FIG. 6 is a timing chart 7 of a task period 7a and a rest period 7b used when a cold stimulus is applied to the subject P, and a graph 8 showing a temporal change in the intensity of the cold stimulus.

In the first embodiment, as shown in the timing chart 7 of FIG. 6, the task period 7a in which the ice pack 5 is applied to the left palm 6a of the subject P, and the rest period 7b in which the subject P closes his or her eyes and is kept at rest are set as one set, and five sets in total are repeated. The task period 7a is 15 seconds, for example. The rest period 7b is 15 seconds, for example. The left palm 6a of the subject P is cooled by the ice pack 5 and the cooling effect is maintained (accumulated) such that the relative intensity of a stimulus 5a applied by the ice pack 5 increases each time the task is repeated. That is, as shown in the graph 8 of FIG. 8, in the task period 7a, the intensity of the cold stimulus increases with time. In the rest period 7b, the intensity of the cold stimulus decreases, but the cold stimulus does not disappear. In the next task period 7a, the intensity of the cold stimulus increases again, and the intensity of the cold stimulus gradually increases. The stimulus 5a applied by the ice pack 5 is an example of a "cool stimulus" in the claims.

(Method for Determining Cognitive Function of Subject)

In the first embodiment, the degree of the cognitive function of the subject P is determined based on a change in the cerebral blood flow of the subject P occurring when the stimulus 5a is applied to the subject 5 by the ice pack 5. According to a first example described below, the cold stimulus is applied a plurality of times such that an ROI that was effective when the degree of the cognitive function of the subject P was determined and a tendency of a blood flow change in the ROI were confirmed. In the first example described below, an ROI 3 (see FIG. 2) was confirmed as the ROI that was effective when the degree of the cognitive function of the subject P was determined. In the first embodiment, the degree of the cognitive function of the subject P is determined by comparing the tendency of the change in the cerebral blood flow of the subject P in the ROI 3 with the experimental results obtained in the first example.

First Example

An experiment for obtaining an index for determining the degree of the cognitive function of the subject P according to the first example is now described with reference to FIGS. 7(A) to 7(C).

In the first example, subjects P were divided into three groups, which were non-demented persons (hereinafter referred to as NDCs), persons with mild cognitive impairment (hereinafter referred to as MCIs), and Alzheimer's patients (hereinafter referred to as ADs) from 60 to 84 years old, and the brain activity of each group was measured. Then, the measurement results of the brain activity of these groups were compared such that the tendency of the brain activity that differed depending on the degree of the cognitive function of each of the subjects P was acquired. The number of subjects P who performed this task was twenty-two for the NDCs, twenty-seven for the MCIs, and twenty-two for the ADs. Note that there was no significant difference in average age between the groups.

In the first example, when a task of applying a cold stimulus to the left palm 6a of each of the subjects P was performed, a change in the cerebral blood flow of the subject P was acquired by the brain activity measurement device 1, and the degree of the cognitive function of the subject P was determined based on the acquired change in the cerebral blood flow. As a method for determining the degree of the cognitive function, in each channel shown in FIG. 2, a difference between the mean cerebral blood flow for 5 seconds before the start of the task and the mean cerebral blood flow for 15 seconds in the task period 7a was determined each time the task was repeated, and was used as a feature amount. Then, the feature amount was compared in each of the subject groups (NDCs, MCIs, and ADs) for each repetition count. As a comparison method, a significant difference test was performed by a paired t-test for a relative combination pair between task repetitions.

FIGS. 7(A) to 7(C) are diagrams showing analysis results 10 of the t-test for each subject group. FIG. 7(A) shows analysis results 10a of the t-test of the NDCs. FIG. 7(B) shows analysis results 10b of the t-test of the MCIs. FIG. 7(C) shows analysis results 10c of the t-test of the ADs. The vertical axis of each view shown in FIGS. 7(A) to 7(C) indicates the mean amount of change in cerebral blood flow, and a plot 11 shows the mean value of change in the cerebral blood flow of the subjects P. Straight lines 12a and 12b indicate plus and minus standard deviations, respectively. A mark "*" in FIGS. 7(A) to 7(C) indicates that the significance level is 5% or less. A mark "**" in FIGS. 7(A) to 7(C) indicates that the significance level is 1% or less.

As a result of the analysis of each channel, in the first example, results having a significant difference were obtained in the measurement data of the ROI3 (see FIG. 2). Specifically, in the NDCs, a first task was compared with a third task, and the first task was compared with a fifth task such that a significant difference p<0.01 (significance level of 1% or less) was observed. Furthermore, in the NDCs, the first task was compared with a fourth task such that a significant difference p<0.05 (significance level of 5% or less) was observed. On the other hand, in the MCIs and the ADs, no significant difference was observed between the tasks. Thus, when the task of applying the cold stimulus to the subjects P a plurality of times was performed, a result that the NDCs could be distinguished from the MCIs and the ADs was obtained when in the ROI3, the feature amount obtained in the first task was larger than the feature amounts obtained in the third, fourth, and fifth tasks.

Advantages of First Embodiment

According to the first embodiment, the following advantages are obtained.

According to the first embodiment, as described above, the method for determining the cognitive function of the subject P includes step S1 of applying the load including the sensory stimulus to the sensory body of the subject P a plurality of times, or applying the load including the tasks with different degrees of difficulty to the subject P a plurality of times. In addition, the method for determining the cognitive function of the subject P includes step S2 of measuring a change in the brain activity of the subject P when the load is applied in step S1 of applying the load a plurality of times, and acquiring the measurement data. Furthermore, the method for determining the cognitive function of the subject P includes step S3 of determining the degree of the cognitive function of the subject P based on the amount of change in the measurement data. Accordingly, when the load including the sensory stimulus is applied to the sensory body of the subject P a plurality of times, a change in brain activity can be measured due to the sensory stimulus that does not require understanding of a cognitive task without depending on an individual difference in adaptation to the cognitive task. When the load including the tasks with different degrees of difficulty is applied to the subject P a plurality of times, a change in brain activity due to the task with a degree of difficulty according to the subject P can be measured. Consequently, the degree of the cognitive function can be determined even when there is an individual difference in adaptation of the subject P to the cognitive task.

According to the first embodiment, as described above, when the sensory stimulus is applied a plurality of times, the sensory stimulus to be applied to the subject P is a persistent stimulus. Accordingly, as the number of times the stimulus is applied to the subject P increases, the influence of the stimulus is accumulated (remains), and thus the relative intensity of the stimulus can be gradually increased. Consequently, the degree of the cognitive function can be determined based on a relative change in the brain activity of the subject P with respect to the stimulus accumulated as the number of times the stimulus is applied increases.

According to the first embodiment, as described above, the persistent stimulus is a stimulus given persistence by applying a sensory stimulus while the influence of the previous stimulus remains when the sensory stimulus is applied to the subject P. Accordingly, it is easy to gradually increase the relative intensity of the sensory stimulus. Even when there is an individual difference in sensitivity to the sensory stimulus, the response to the intensity change of the sensory stimulus can be measured.

According to the first embodiment, as described above, the persistent stimulus is a cold stimulus. Accordingly, in comparison with a warm stimulus, for example, a stimulus can be applied to the subject P using a cold stimulus having more receptors for the stimulus. Consequently, a change in more active brain activity can be measured.

According to the first embodiment, as described above, the sensory body is the hand 6 of the subject P, and the sensory stimulus is a contact stimulus. Accordingly, the stimulus can be applied by directly touching the hand with high sensitivity to the stimulus. Consequently, a more accurate change in brain activity can be measured.

According to the first embodiment, as described above, in step S2 of acquiring the measurement data, the measurement sites are set within the range including any of F3, F4, P3, and P4 in accordance with the International 10-20 system. Accordingly, the measurement sites for measuring the brain activity can be made substantially constant. Consequently, the occurrence of errors in the measurement data due to different measurement sites can be significantly reduced or prevented. Furthermore, as a result of measuring a change in the brain activity of the subject P by applying the cold stimulus, a significant change in brain activity with respect to the load has been confirmed in any of F3, F4, P3, and P4. Therefore, the degree of the cognitive function can be determined with a significant degree of accuracy.

According to the first embodiment, as described above, the step of acquiring measurement data includes measuring a change in the cerebral blood flow of the subject P as a change in brain activity by the near-infrared spectroscopy. Accordingly, a change in the brain activity of the subject P can be measured by the brain activity measurement device 1. Consequently, the brain activity measurement device 1 is non-invasive, and does not require large-scale equipment as compared with MRI, for example, and thus a change in the brain activity of the subject P can be easily measured.

Second Embodiment

A cognitive function determination method according to a second embodiment of the present invention is now described with reference to FIGS. 4 and 8. In the second embodiment, in step S1 of applying a load to a subject P a plurality of times, tasks related to calculation with different degrees of difficulty are given to the subject P a plurality of times, unlike the first embodiment in which the cold stimulus is applied to the subject P a plurality of times in step S1 of applying the load to the subject P a plurality of times. The same configurations as those of the first embodiment are denoted by the same reference numerals, and description thereof is omitted.

(Step of Giving Tasks Related to Calculation with Different Degrees of Difficulty Plurality of Times)

In the second embodiment, the tasks with different degrees of difficulty are tasks related to calculation. In the second embodiment, step S1 of giving the tasks with different degrees of difficulty a plurality of times includes repeatedly presenting, to the subject P, the tasks related to calculation with different degrees of difficulty. Furthermore, in the second embodiment, when the tasks with different degrees of difficulty are given a plurality of times, the degrees of difficulty of the tasks are set such that the degree of difficulty of a second task given after a first task is higher than the degree of difficulty of the first task.

FIG. 8 is a timing chart 20 of a task period 20a and a rest period 20b used when tasks related to calculation with different degrees of difficulty are given to the subject P, and a graph 21 showing a temporal change in the degrees of difficulty of the tasks related to calculation. In the second embodiment, as shown in the timing chart 20 of FIG. 8, the task period 20a in which the subject P is made to perform a calculation, and the rest period 20b in which the subject P is made to pronounce a meaningless word before and after the task period 20a (a pre-rest period and a post-rest period) are set as one set, and the subject P is made to work a total of five sets of problems. In the pre-rest period and the post-rest period, a meaningless word is pronounced to construct a baseline for measuring a cerebral blood flow change. The task period 20a is 20 seconds, for example. The pre-rest period and the post-rest period are each 20 seconds, for example. The meaningless word that the subject P pronounces during the pre-rest period and the post-rest period is "a, i, u, e, o", for example.

As shown in the graph 21, the degree of difficulty of a calculation problem is different for each set, and the degree of difficulty of the problem to be performed later is set higher. As the calculation problem, a revised version of the serial seven (100–7) used in a mini-mental state examination (MMSE) for diagnosing dementia can be used, for example. That is, as the tasks related to calculation with different degrees of difficulty, a problem of continuously subtracting 2 from 100 (100–2), a problem of continuously subtracting 3 from 100 (100–3), a problem of continuously subtracting 7 from 100 (100–7), a problem of continuously subtracting 7 from 101 (101–7), and a problem of continuously subtracting 7 from 102 (102–7) are set. Note that in the subtraction of an even number and the subtraction of an odd number, the degree of difficulty of the subtraction of an even number is lower.

(Method for Determining Cognitive Function of Subject)

In the second embodiment, the degree of the cognitive function of the subject P is determined based on a change in the cerebral blood flow of the subject P when the tasks related to calculation with different degrees of difficulty are given to the subject P. According to a second example described below, the tasks related to calculation with different degrees of difficulty were given to the subject P a plurality of times such that an ROI that was effective when the degree of the cognitive function of the subject P was determined and a tendency of a blood flow change in the ROI were confirmed. In the second example described below, an ROI 2 (see FIG. 2) was confirmed as the ROI that was effective when the degree of the cognitive function of the subject P was determined. In the second embodiment, the degree of the cognitive function of the subject P is determined by comparing the tendency of the change in the cerebral blood flow of the subject P in the ROI 2 with the experimental results obtained in the second example.

The remaining configurations of the second embodiment are similar to those of the aforementioned first embodiment.

Second Example

An experiment for obtaining an index for determining the degree of the cognitive function of the subject P according to the second example is now described with reference to FIGS. 9(A) to 9(c).

In the second example, as in the first example described above, subjects P were divided into three groups, which were NDCs, MCIs, and ADs from 60 to 84 years old, and the brain activity of each group was measured. Then, the measurement results of the brain activity of these groups were compared such that the tendency of the brain activity that differed depending on the degree of the cognitive function of each of the subjects P was acquired. The number of subjects P who performed these tasks was twenty-two for the NDCs, twenty-seven for the MCIs, and twenty-two for the ADs.

In the second example, the tasks related to calculation used in the second embodiment were given to the subjects P, and changes in the cerebral blood flow of the subjects P at that time were measured. In the second example, a method for determining the degree of the cognitive function is the same as in the first example, and a difference between the mean cerebral blood flow for 5 seconds before the start of the task and the mean cerebral blood flow for 20 seconds in the task period 20a was determined each time the task was repeated, and was used as a feature amount. Then, the feature amount was compared in each of the subject groups (NDCs, MCIs, and ADs) for each calculation problem. As a comparison method, a significant difference test was performed by a paired t-test for a relative combination pair between task repetitions.

FIGS. 9(A) to 9(c) are diagrams showing analysis results 22 of the t-test for each subject group. FIG. 9(A) shows analysis results 22a of the t-test of the NDCs. FIG. 9(B) shows analysis results 22b of the t-test of the MCIs. FIG. 9(C) shows analysis results 22c of the t-test of the ADs. The vertical axis of each view shown in FIGS. 9(A) to 9(c) indicates the mean amount of change in cerebral blood flow, and a plot 23 shows the mean value of change in the cerebral blood flow of the subjects P. Straight lines 24a and 24b indicate plus and minus standard deviations, respectively.

As a result of the analysis of each channel, in the second example, results having a significant difference were obtained in the measurement data of the ROI2 (see FIG. 2). Specifically, in the NDCs, a first problem was compared with a second problem such that a significant difference $p<0.01$ (significance level of 1% or less) was observed. In the MCIs, the first problem was compared with the second problem, and the first problem was compared with a fourth problem such that a significant difference $p<0.01$ (significance level of 1% or less) was observed. Furthermore, in the NDCs, the first problem was compared with the fourth problem, and the first problem was compared with a fifth problem such that a significant difference $p<0.05$ (significance level of 5% or less) was observed. In the MCIs, the second problem was compared with a third problem such that a significant difference $p<0.05$ (significance level of 5% or less) was observed. On the other hand, in the ADs, no significant difference was observed. Thus, when the tasks related to calculation were used, a result that the NDCs and the MCIs could be distinguished from the ADs was obtained when in the ROI2, the feature amounts of the first problem and the second problem were large.

Advantages of Second Embodiment

According to the second embodiment, the following advantages are obtained.

According to the second embodiment, as described above, step S1 of giving the tasks with different degrees of difficulty a plurality of times includes repeatedly presenting, to the subject P, the tasks related to calculation with different degrees of difficulty. Accordingly, the possibility that the subject P memorizes an answer to the calculation problem due to repeating the same problem can be significantly reduced or prevented. In addition, the subject P can be accustomed to the tasks by performing the tasks related to calculation with different degrees of difficulty a plurality of times, and thus the possibility that the subject P stops the tasks halfway can be significantly reduced or prevented. Furthermore, the subject P can be made to execute a task with a degree of difficulty suitable for the subject P by performing the tasks related to calculation with different degrees of difficulty a plurality of times. Consequently, the degree of cognitive function related to calculation can be obtained as the index for determining the degree of the cognitive function of the subject P, and thus the accuracy of determining the degree of the cognitive function can be improved.

According to the second embodiment, as described above, when the tasks with different degrees of difficulty are given a plurality of times, the degrees of difficulty of the tasks are set such that the degree of difficulty of the second task given after the first task is higher than the degree of difficulty of the first task. Accordingly, the subject P can be accustomed to the tasks using the task with a low degree of difficulty. Consequently, the possibility that the subject P gives up executing the tasks halfway can be significantly reduced or prevented. In addition, the tasks with different degrees of difficulty are given a plurality of times such that the subject P can be made to execute a task with a degree of difficulty suitable for the subject P, and thus failure to detect brain activity can be significantly reduced or prevented.

The remaining advantages of the second embodiment are similar to those of the aforementioned first embodiment.

Third Embodiment

A cognitive function determination method according to a third embodiment is now described with reference to FIGS. 4 and 10 to 12. In the third embodiment, in step S1 of applying a load to a subject P a plurality of times, tasks related to memory and imagination with different degrees of difficulty are given to the subject P a plurality of times, unlike each of the first and second embodiments in which the cold stimulus or the tasks related to calculation with different degrees of difficulty are given to the subject P a plurality of times in step S1 of applying the load to the subject P a plurality of times. The same configurations as those of the first and second embodiments are denoted by the same reference numerals, and description thereof is omitted.

(Step of Giving Tasks Related to Memory and Imagination with Different Degrees of Difficulty Plurality of Times)

In the third embodiment, step S1 of giving the tasks with different degrees of difficulty a plurality of times includes repeatedly presenting, to the subject P, the tasks in combination of memory with imagination with different degrees of difficulty. Furthermore, in the third embodiment, when the tasks with different degrees of difficulty are given a plurality of times, the degrees of difficulty of the tasks are set such that the degree of difficulty of a second task given after a first task is higher than the degree of difficulty of the first task.

Figure 10:
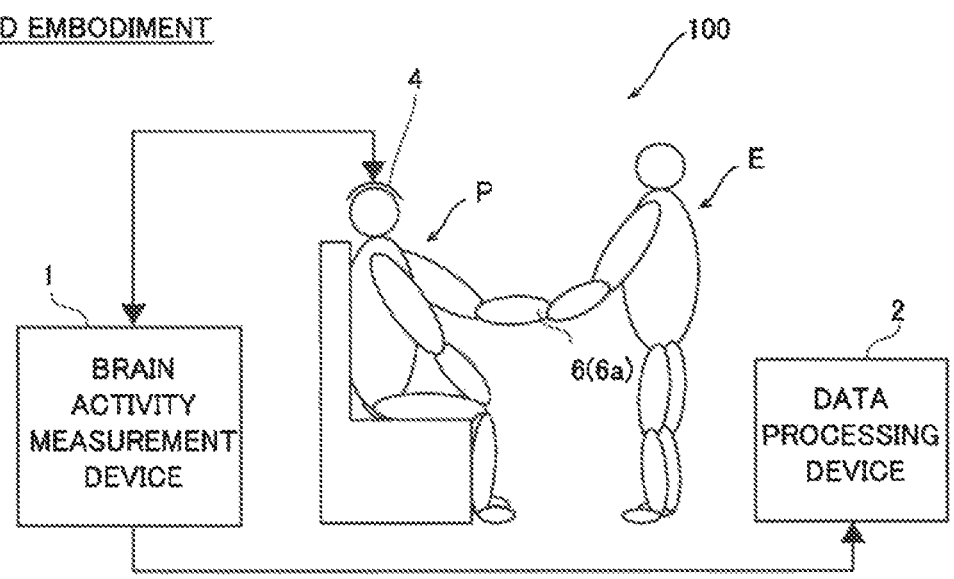
FIG. 10 is a schematic view for illustrating a method for applying a task related to memory and imagination to a subject according to a third embodiment of the present invention.
Figure 11:
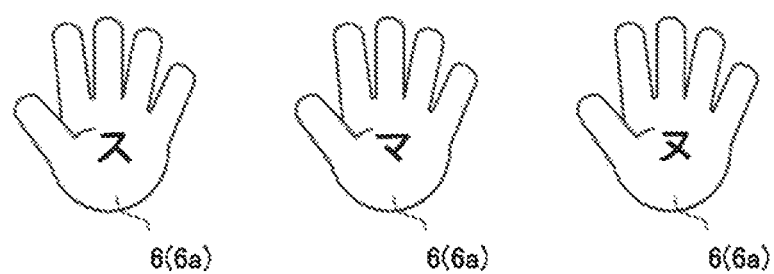
FIG. 11 is a schematic view for illustrating the task related to memory and imagination to the subject according to the third embodiment of the present invention.

FIG. 10 is a schematic view showing when the tasks related to memory and imagination are given to the subject P. FIG. 11 is a schematic view showing an example of the tasks related to memory and imagination. In the third embodiment, as shown in FIG. 10, an approach in which an experimenter E writes characters with similar shapes on the hand 6 of the subject P, and the subject P guesses the characters is repeatedly presented for each degree of difficulty. Specifically, the experimenter E successively writes two or three characters from three characters with similar shapes on the left palm 6a of the subject P who closes his or her eyes with his or her finger.

Figure 12:
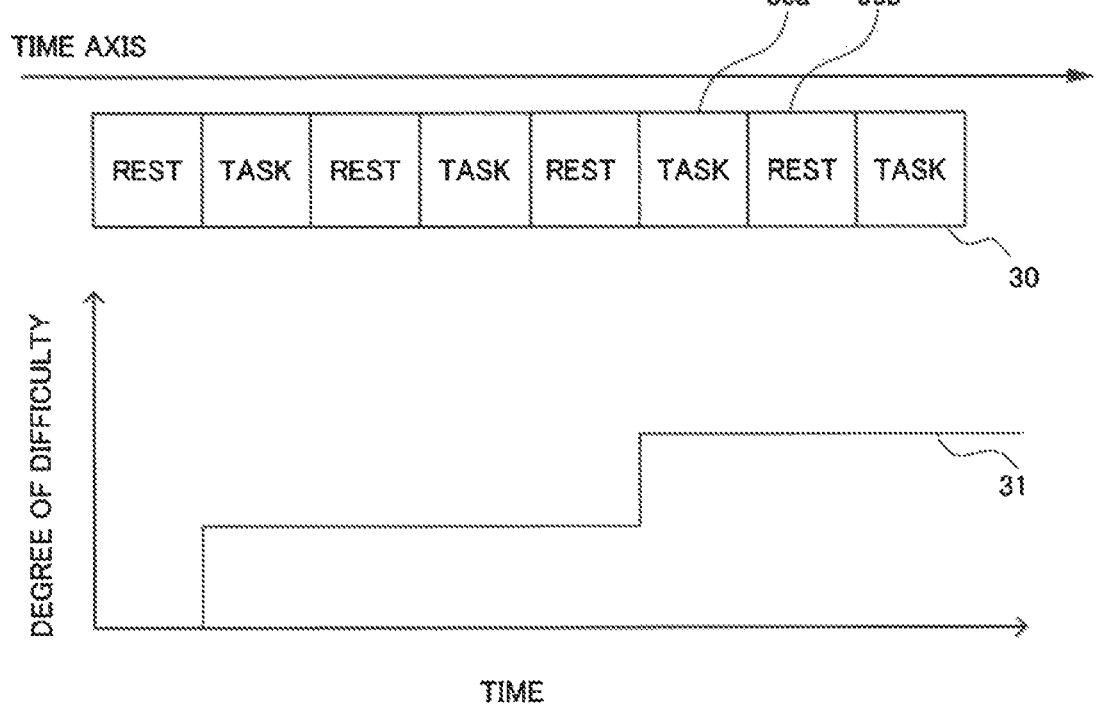
FIG. 12 is a timing chart of a task and a rest, and a graph showing a temporal change in the degree of difficulty of the task according to the third embodiment of the present invention.

FIG. 12 is a timing chart 30 of a task period 30a and a rest period 30b used when the tasks related to memory and imagination with different degrees of difficulty are given to the subject P, and a graph 31 showing a temporal change in the degrees of difficulty of the tasks related to memory and imagination. The task period 30a is a period in which characters with similar shapes are written on the subject P. The rest period 30b is provided before and after the task period 30a, and is a period in which the subject P closes his or her eyes and is relaxed. The rest period 30b before a task is defined as a pre-rest period. The rest period 30b after a task is defined as a post-rest period. In the pre-rest period and the post-rest period, a baseline for measuring a cerebral blood flow change is constructed. The task period 30a is 15 seconds, for example. The pre-rest period and the post-rest period are each 20 seconds, for example. The characters with similar shapes are Japanese katakana characters "ス", "マ", and "ヌ" shown in FIG. 11, for example.

The degrees of difficulty of the tasks are set such that the degree of difficulty of a task performed later is higher than that of a task performed earlier, as shown in the graph 31 in FIG. 12. That is, a first task of writing two characters is performed twice, and then a second task of writing three characters is performed twice in order to make the degrees of difficulty of the tasks different. Although the task time is the same, the degree of difficulty is increased by increasing the number of characters to be written on the palm 6a from two to three.

(Method for Determining Cognitive Function of Subject)

In the third embodiment, the degree of the cognitive function of the subject P is determined based on a change in the cerebral blood flow of the subject P occurring when the tasks related to memory and imagination with different degrees of difficulty are given to the subject P. According to a third example described below, the tasks related to memory and imagination with different degrees of difficulty were given a plurality of times such that a channel that was effective when the degree of the cognitive function of the subject P was determined and a tendency of a blood flow change in the channel were confirmed. In the third example described below, it has been confirmed that blood flow changes in four channels, which are a channel 10, a channel 37, a channel 45, and a channel 53 shown in FIG. 2, are indexes that are effective when the degree of the cognitive function of the subject P is determined. In the third embodiment, the degree of the cognitive function of the subject P is determined by comparing the tendency of the change in the cerebral blood flow of the subject P in each of these four channels with the experimental results obtained in the third example.

The remaining configurations of the third embodiment are similar to those of the aforementioned first embodiment.

Third Example

An experiment for obtaining an index for determining the degree of the cognitive function of the subject P according to the third example is now described with reference to FIGS. 13(A) to 13(D).

In the third example, as in the first and second examples described above, subjects P were divided into three groups, which were NDCs, MCIs, and ADs from 60 to 84 years old, and the brain activity of each group was measured. Then, the measurement results of the brain activity of these groups were compared such that the tendency of the brain activity that differed depending on the degree of the cognitive function of each of the subjects P was acquired. The number of subjects P who performed these tasks was twenty-one for the NDCs, eighteen for the MCIs, and ten for the ADs.

In the third example, the task of writing characters with similar shapes on the hand 6 of the subject P used in the third embodiment was given to the subjects P a plurality of times, and changes in the cerebral blood flow of the subjects P at that time were measured. In the third example, in a method for determining the degree of the cognitive function, a difference between the mean cerebral blood flow for 5 seconds before the start of the task and the mean cerebral blood flow in the task period 30a was determined each time the task was repeated, and the mean of all differences determined during these repetitions was used as a feature amount. Then, LASSO analysis was performed on the feature amount in each disease group. Then, as a result of the LASSO analysis, channels that contribute to distinguishing between two groups with respect to the amount of change in each channel (see FIG. 2) were selected. Then, for the selected channels, a significant difference test between the two groups was performed by the Mann-Whitney U test.

A Box chart of disease groups for each channel was created by the significant difference test, and changes in cerebral blood flow between the diseases were confirmed. FIGS. 13(A) to (13(D) show examples of box charts of analysis results 32 obtained when the tasks related to memory and imagination are performed. FIG. 13(A) shows analysis results 32a of the channel 10. FIG. 13(B) shows analysis results 32b of the channel 37. FIG. 13(C) shows analysis results 32c of the channel 45. FIG. 13(D) shows analysis results 32d of the channel 53. The vertical axis of each view in FIGS. 13(A) to 13(D) indicates the amount of change in cerebral blood flow. Black circle 33 in FIGS. 13(A) to 13(D) are plots showing the feature amount of each subject P. Triangles 34a and 34b in FIGS. 13(A) to 13(D) are the maximum value and the minimum value of the feature amounts of the subjects P, respectively. A thick line 36 in a box 35 is the median value of the feature amounts of the subjects P, and a thin line 37 in the box 35 is the mean value of the feature amounts of the subjects P. Lines 38a and 38b above and below the box 35 are plus and minus 1.5 SDs (standard deviations) of the feature amounts of the subjects P, respectively. The ranges of plus and minus 1.5 SDs include about 87% of the feature amounts of the subjects P.

As a result of analysis of all fifty-four channels shown in FIG. 2, in the third example, nine channels that contribute to distinguishing between two groups, the NDCs and the MCIs, were obtained by LASSO analysis, and in four (the channel 10, the channel 37, the channel 45, and the channel 53) of the nine channels, significant differences were observed by the Mann-Whitney U test. In addition, six channels that contribute to distinguishing between two groups, the MCIs and the ADs, were obtained by LASSO analysis, and a significant difference was observed in one (channel 37) of the six channels by the Mann-Whitney U test. As shown in FIGS. 13(A) to 13(D), there was a tendency that the cerebral blood flow increased from the NDCs to the MCIs, and decreased from the MCIs to the ADs.

Advantages of Third Embodiment

According to the third embodiment, the following advantages are obtained.

According to the third embodiment, as described above, step S1 of giving the tasks with different degrees of difficulty a plurality of times includes repeatedly presenting, to the subject P, the tasks in combination of memory with imagination with different degrees of difficulty. Accordingly, the subject P can be accustomed to the tasks by performing the tasks in combination of memory with imagination with different degrees of difficulty a plurality of times, and thus the possibility that the subject P stops the tasks halfway can be significantly reduced or prevented. Furthermore, the subject P can be made to execute a task with a degree of difficulty suitable for the subject P by performing the tasks related to memory and imagination with different degrees of difficulty a plurality of times. Consequently, the degree of cognitive function related to memory and imagination can be obtained as the index for determining the degree of the cognitive function of the subject P, and thus the accuracy of determining the degree of the cognitive function can be improved.

The remaining advantages of the third embodiment are similar to those of the aforementioned first embodiment.

Fourth Embodiment

A cognitive function determination method according to a fourth embodiment is now described with reference to FIGS. 4 and 14 to 16. In the fourth embodiment, in step S1 of applying a load to a subject P a plurality of times, tasks related to spatial recognition with different degrees of difficulty are given to the subject P a plurality of times, unlike each of the first to third embodiments in which the cold stimulus, the tasks related to calculation with different degrees of difficulty, or the tasks related to memory and imagination with different degrees of difficulty are given to the subject P a plurality of times in step S1 of applying the load to the subject P a plurality of times. The same configurations as those of the first to third embodiments are denoted by the same reference numerals, and description thereof is omitted.

(Step of Giving Tasks Related to Spatial Recognition with Different Degrees of Difficulty Plurality of Times)

Figure 14:
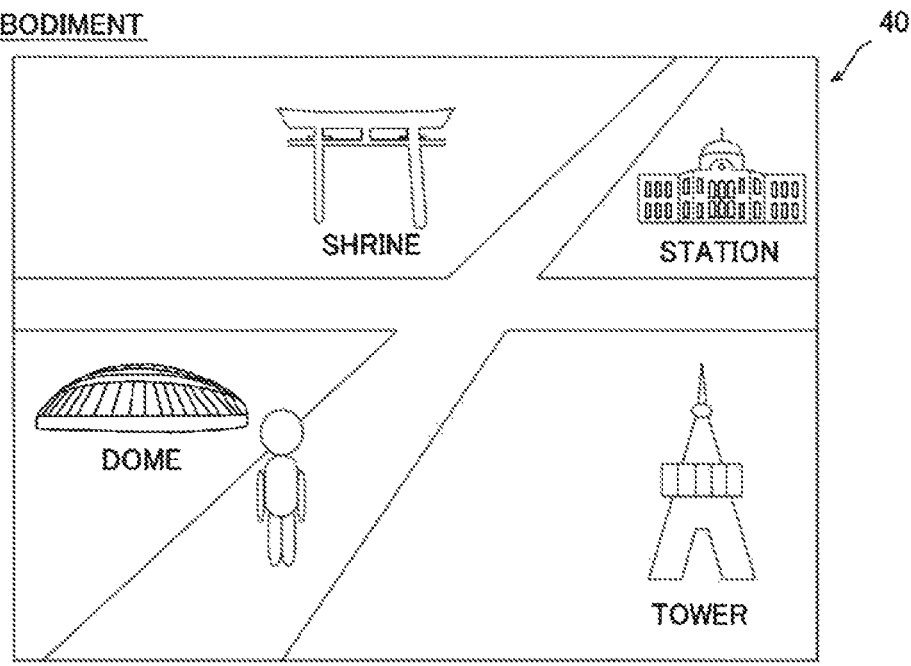
FIG. 14 is a schematic view for illustrating a method for applying a task related to spatial recognition to a subject according to a fourth embodiment of the present invention.
Figure 15:
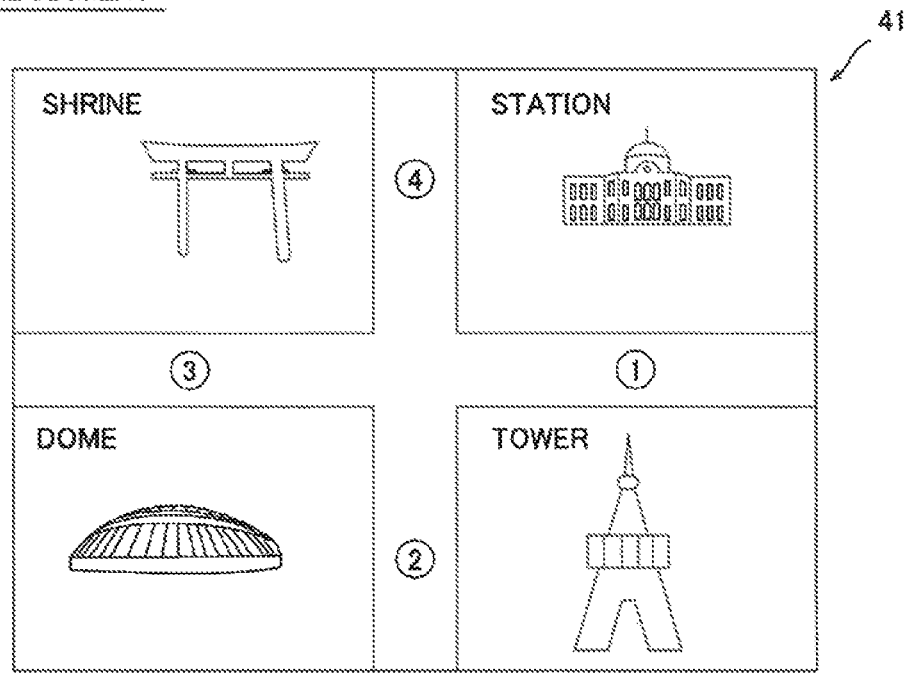
FIG. 15 is a schematic view for illustrating the task related to spatial recognition applied to the subject according to the fourth embodiment of the present invention.

FIG. 14 is a schematic view showing an example of a landscape photograph 40 displayed on a display device 3 when the tasks related to spatial recognition are given to the subject P. FIG. 15 is a schematic view showing an example of a map 41 confirmed by the subject P when the subject P answers the tasks related to spatial recognition.

In the fourth embodiment, with regard to the tasks related to spatial recognition, step S1 of giving the tasks with different degrees of difficulty a plurality of times includes repeatedly presenting, to the subject P, the tasks related to spatial recognition with different degrees of difficulty. Furthermore, in the fourth embodiment, when the tasks with different degrees of difficulty are given a plurality of times, the degrees of difficulty of the tasks are set such that the degree of difficulty of a second task given after a first task is higher than the degree of difficulty of the first task.

In the fourth embodiment, as shown in FIG. 14, the display device 3 displays the landscape photograph 40 in which a person is standing at an intersection and different buildings are respectively located at corners of the intersection. The subject P is handed the map 41 (see FIG. 15) showing a schematic view of the buildings, for example, drawn in the landscape photograph 40 shown in FIG. 14 and answers where the subject P should stand to see the landscape of the landscape photograph 40 shown in FIG. 14 with a number. After the way is explained in advance, the tasks are executed. The landscape photograph 40 and the map 41 are examples of a "task related to spatial recognition" in the claims.

FIG. 16 is a timing chart 42 of a task period 42a and a rest period 42b used when the tasks related to spatial recognition with different degrees of difficulty are given to the subject P, and a graph 43 showing a temporal change in the degrees of difficulty of the tasks related to spatial recognition. A pre-rest period and a post-rest period are provided before and after the task period 42a, respectively. The task period 42a is 30 seconds, for example. The pre-rest period and the post-rest period are each 20 seconds, for example. During the pre-rest period and the post-rest period, the subject P is made to pronounce a meaningless word ("a, i, u, e, o", for example). The meaningless word is pronounced such that a baseline for measuring a cerebral blood flow change is constructed.

In the fourth embodiment, as shown in the graph 43 of FIG. 16, the first and second tasks are set to have a lower degree of difficulty, and third and fourth tasks are set to have a higher degree of difficulty. Specifically, the degree of difficulty of the task is increased by changing the arrangement of the buildings and increasing the number of roads and the number of buildings, for example, and the task is executed a plurality of times.

(Method for Determining Cognitive Function of Subject)

In the fourth embodiment, the degree of the cognitive function of the subject P is determined based on a change in the cerebral blood flow of the subject P occurring when the tasks related to spatial recognition with different degrees of difficulty are given to the subject P. According to a fourth example described below, the tasks related to spatial recognition with different degrees of difficulty were given a plurality of times such that a channel that was effective when the degree of the cognitive function of the subject P was determined and a tendency of a blood flow change in the channel were confirmed. In the fourth example described below, it has been confirmed that blood flow changes in three channels, which are a channel 2, a channel 32, and a channel 52 shown in FIG. 2, are indexes that are effective when the degree of the cognitive function of the subject P is determined. In the fourth embodiment, the degree of the cognitive function of the subject P is determined by comparing the tendency of the change in the cerebral blood flow of the subject P in each of these three channels with the experimental results obtained in the fourth example.

The remaining configurations of the fourth embodiment are similar to those of the aforementioned first embodiment.

Fourth Example

An experiment for obtaining an index for determining the degree of the cognitive function of the subject P according to the fourth example is now described with reference to FIGS. 17(A) to 17(C).

In the fourth example, as in the first to third examples described above, subjects P were divided into three groups, which were NDCs, MCIs, and ADs from 60 to 84 years old, and the brain activity of each group was measured. Then, the measurement results of the brain activity of these groups were compared such that the tendency of the brain activity that differed depending on the degree of the cognitive function of each of the subjects P was acquired. The number of subjects P who performed these tasks was twenty-one for the NDCs, eighteen for the MCIs, and ten for the ADs.

In the fourth example, the tasks related to spatial recognition with different degrees of difficulty were given to the subjects P a plurality of times, and changes in the cerebral blood flow of the subjects P at that time were measured. In the fourth example, in a method for determining the degree of the cognitive function, a difference between the mean cerebral blood flow for 5 seconds before the start of the task and the mean cerebral blood flow in the task period 42a was determined each time the task was repeated, and the mean of all differences determined during these repetitions was used as a feature amount. Then, LASSO analysis was performed on the feature amounts in the NDCs and the MCIs, in the NDCs and the ADs, and in the MCIs and the ADs, channels that contribute to distinguishing between the two groups with respect to the amount of change in each channel (see FIG. 2) were selected, and in the selected channels, a significant difference test between the two groups was performed by the Mann-Whitney U test.

A Box chart of disease groups for each channel was created by the significant difference test, and changes in cerebral blood flow between the diseases were confirmed. FIGS. 17(A) to 17(C) are schematic views showing examples of box charts of analysis results 44 obtained when the tasks related to spatial recognition are performed. FIG. 17(A) shows analysis results 44a of the channel 2. FIG. 17(B) shows analysis results 44b of the channel 32. FIG. 17(C) shows analysis results 44c of the channel 52. The vertical axis of each view in FIGS. 17(A) to 17(C) indicates the amount of change in cerebral blood flow. A black circle 45 in FIGS. 17(A) to 17(C) is a plot showing the feature amount of each subject P. Triangles 46a and 46b in FIGS. 17(A) to 17(C) are the maximum value and the minimum value of the feature amounts of the subjects P, respectively. A thick line 48 in a box 47 is the median value of the feature amounts of the subjects P, and a thin line 49 in the box 47 is the mean value of the feature amounts of the subjects P. Lines 50a and 50b above and below the box 47 are plus and minus 1.5 SDs (standard deviations) of the feature amounts of the subjects P, respectively.

As a result of analysis of all fifty-four channels shown in FIG. 2, in the fourth example, nine channels that contribute to distinguishing between two groups, the NDCs and the ADs, were obtained by LASSO analysis, and in three (the channel 2, the channel 32, and the channel 52) of the nine channels, significant differences were observed by the Mann-Whitney U test. As shown in FIGS. 17(A) to 17(C), there was a tendency that the cerebral blood flow increased from the NDCs to the MCIs and the ADs in this order.

Advantages of Fourth Embodiment

According to the fourth embodiment, the following advantages are obtained.

According to the fourth embodiment, as described above, step S1 of giving the tasks with different degrees of difficulty a plurality of times includes repeatedly presenting, to the subject P, the tasks related to spatial recognition with different degrees of difficulty. Accordingly, the subject P can be accustomed to the tasks by performing the tasks related to spatial recognition with different degrees of difficulty a plurality of times, and thus the possibility that the subject P stops the tasks halfway can be significantly reduced or prevented. Furthermore, the subject P can be made to execute a task with a degree of difficulty suitable for the subject P by performing the tasks related to spatial recognition with different degrees of difficulty a plurality of times. Consequently, the degree of cognitive function related to spatial recognition can be obtained as the index for determining the degree of the cognitive function of the subject P, and thus the accuracy of determining the degree of the cognitive function can be improved.

The remaining advantages of the fourth embodiment are similar to those of the aforementioned first embodiment.

Fifth Embodiment

Figure 18:
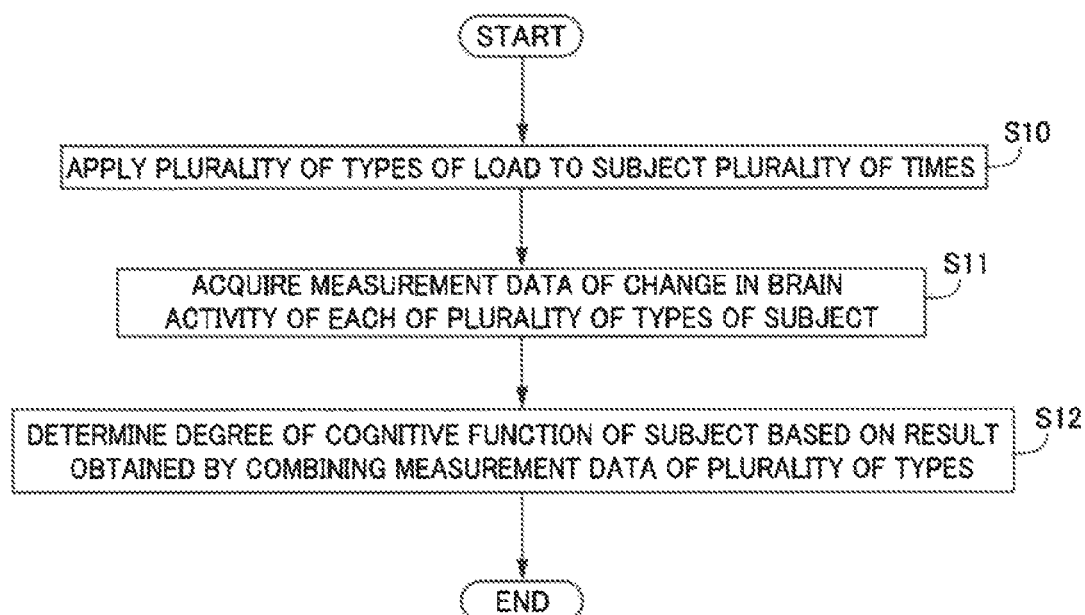
FIG. 18 is a flowchart showing a flow of determining the degree of subject's cognitive function according to a fifth embodiment of the present invention.

A cognitive function determination method according to a fifth embodiment is now described with reference to FIGS. 1 and 18.

In the fifth embodiment, in step S10 (see FIG. 18) of applying loads to a subject P a plurality of times, a plurality of types among a sensory stimulus and tasks with different degrees of difficulty are applied to the subject P a plurality of times, unlike each of the first to fourth embodiments in which any one type among the sensory stimulus and the tasks with different degrees of difficulty is applied to the subject P a plurality of times in step S1 (see FIG. 1) of applying the load to the subject P a plurality of times. The same configurations as those of the first to fourth embodiments are denoted by the same reference numerals, and description thereof is omitted.

In the fifth embodiment, the tasks with different degrees of difficulty are tasks related to at least one of calculation, a combination of memory and imagination, and spatial recognition. A method for determining the degree of the cognitive function of the subject P includes step S10 of giving each of the plurality of types among the sensory stimulus and the tasks with different degrees of difficulty to the subject P a plurality of times. In addition, the method for determining the degree of the cognitive function of the subject P includes step S11 of measuring a change in the brain activity of the subject P when the sensory stimulus or the tasks are given in step S10 of giving each of the plurality of types among the sensory stimulus and the tasks a plurality of times, and acquiring the measurement data of each of the plurality of types. Furthermore, the method for determining the degree of the cognitive function of the subject P includes step S12 of determining the degree of the cognitive function of the subject P based on a result obtained by combining the amount of change in the measurement data of each of the plurality of types acquired when each of the plurality of types among the sensory stimulus and the tasks with different degrees of difficulty is given. Through these steps, the degree of the cognitive function of the subject P is determined.

In the fifth embodiment, in step S10, the plurality of types among the sensory stimulus and the tasks given to the subject P may be a combination of two types, a combination of three types, or a combination of all four types.

The remaining configurations of the fifth embodiment are similar to those of the aforementioned first to fourth embodiments.

Advantages of Fifth Embodiment

According to the fifth embodiment, the following advantages are obtained.

According to the fifth embodiment, as described above, the tasks with different degrees of difficulty are tasks related to at least one of calculation, a combination of memory and imagination, and spatial recognition. Furthermore, the method for determining the degree of the cognitive function of the subject P includes step S10 of giving each of the plurality of types among the sensory stimulus and the tasks with different degrees of difficulty to the subject P a plurality of times. In addition, the method for determining the degree of the cognitive function of the subject P includes step S11 of measuring a change in the brain activity of the subject P when the sensory stimulus or the tasks are given in step S10 of giving each of the plurality of types among the sensory stimulus and the tasks a plurality of times, and acquiring the measurement data of each of the plurality of types. Moreover, the method for determining the degree of the cognitive function of the subject P includes step S12 of determining the degree of the cognitive function of the subject P based on the result obtained by combining the amount of change in the measurement data of each of the plurality of types acquired when each of the plurality of types among the sensory stimulus and the tasks with different degrees of difficulty is given. Accordingly, the cognitive function can be determined in a complex manner based on the result obtained by combining the data measured from multiple viewpoints. Consequently, the accuracy of determining the degree of the cognitive function of the subject P can be improved.

The remaining advantages of the fifth embodiment are similar to those of the aforementioned first to fourth embodiments.

Modified Examples

The embodiments and examples disclosed this time must be considered as illustrative in all points and not restrictive. The scope of the present invention is not shown by the above description of the embodiments and examples but by the scope of claims for patent, and all modifications (modified examples) within the meaning and scope equivalent to the scope of claims for patent are further included.

For example, while a cold stimulus is used as the sensory stimulus in the aforementioned first embodiment, the present invention is not limited to this. For example, a warm stimulus or a pain stimulus may be used. However, the number of receptors for a warm stimulus is smaller than the number of receptors for a cold stimulus, and thus it may be difficult to obtain a change in brain activity as compared with a cold stimulus. Furthermore, regarding a pain stimulus, there is a great difference in pain sensation between individuals, and thus it is preferable to use a cold stimulus.

While the example in which the degree of the cognitive function of the subject P is determined based on a change in the cerebral blood flow in the ROI 3 has been shown in the aforementioned first embodiment, the present invention is not limited to this. The degree of the cognitive function of the subject P may be determined based on a change in the cerebral blood flow in any of the channels included in the R013. Alternatively, a change in the cerebral blood flow in a channel around the ROI 3 may be included to determine the degree of the cognitive function of the subject P. As long as a result having a significant difference is obtained, data at any measurement position may be used.

While the example in which when the sensory stimulus is applied a plurality of times, a cold stimulus having a constant intensity equivalent to 4° C. is applied as a persistent sensory stimulus to the subject P a plurality of times has been shown in the aforementioned first embodiment, the present invention is not limited to this. For example, when the sensory stimulus is applied a plurality of times, a plurality of sensory stimuli having at least two levels of intensity may be applied to the subject. Thus, the degree of the cognitive function can be determined based on a relative change in the brain activity of the subject P with respect to stimuli having different intensities. That is, it is not necessary to accumulate the sensory stimulus.

While the example in which when the sensory stimulus is applied a plurality of times, a cold stimulus having a constant intensity equivalent to 4° C. is applied as a persistent sensory stimulus to the subject P a plurality of times has been shown in the aforementioned first embodiment, the present invention is not limited to this. For example, the intensity of the sensory stimulus to be applied to the subject may be increased each time the stimulus is applied. Thus, the intensity of the stimulus increases as the number of times the stimulus is applied to the subject P increases, and thus the degree of the cognitive function can be determined based on a relative change in the brain activity of the subject P with respect to the stimulus intensity. That is, even when the sensory stimulus is not accumulated, it is believed that the same advantage as that of the first embodiment in which the stimulus intensity to be applied to the subject P is increased by accumulating the sensory stimulus is obtained.

While a problem such as 100−2 is used as a task related to calculation in the aforementioned second embodiment, the present invention is not limited to this. For example, a problem of subtracting another number, such as 100−4, may be used, or addition may be used. Any calculation task of four arithmetic operations may be used.

While the example in which the degree of the cognitive function of the subject P is determined based on a change in the cerebral blood flow in the R012 has been shown in the aforementioned second embodiment, the present invention is not limited to this. The degree of the cognitive function of the subject P may be determined based on a change in the cerebral blood flow in any of the channels included in the R012. Alternatively, a change in the cerebral blood flow in a channel around the ROI 2 may be included to determine the degree of the cognitive function of the subject P. As long as a result having a significant difference is obtained, data at any measurement position may be used.

While the example in which as the tasks related to memory and imagination, Japanese katakana characters "ス, マ, ヌ" are written with a finger on the left palm 6*a* of the subject P has been shown in the aforementioned third embodiment, the present invention is not limited to this. For example, Japanese katakana characters "コ, ユ, エ" or "ア, ヤ, マ" may be used. Any characters may be used as long as the shapes of the characters are similar.

While the example in which when the degree of the cognitive function of the subject P is determined, the determination is made using four channels that have been confirmed to be effective has been shown in the aforementioned third embodiment, the present invention is not limited to this. The determination may be made using a combination of any two or more of the four channels. However, as the number of channels for the determination is larger, the accuracy of the determination is improved, and thus it is preferable to make the determination using four channels. Furthermore, as long as a result having a significant difference is obtained, data at any measurement position may be used.

While the example in which when the degree of the cognitive function of the subject P is determined, the determination is made using three channels that have been confirmed to be effective has been shown in the aforementioned fourth embodiment, the present invention is not limited to this. The determination may be made using a combination of any two of the three channels. However, as the number of channels for the determination is larger, the accuracy of the determination is improved, and thus it is preferable to make the determination using three channels. Furthermore, as long as a result having a significant difference is obtained, data at any measurement position may be used.

While the example in which data processing is performed in parallel with brain activity measurement has been shown in each of the aforementioned first to fifth embodiments, the present invention is not limited to this. After the measurement of the brain activity of the subject P is completed, the data processing may be performed collectively.

DESCRIPTION OF REFERENCE NUMERALS

5*a*: stimulus applied by the ice pack 5
6, 6*a*: hand (subject's hand, sensory body)
40: landscape photograph (task related to spatial recognition)
41: map (task related to spatial recognition)

The invention claimed is:
1. A cognitive function determination method comprising:
applying a load including a sensory stimulus to a sensory body of a subject a plurality of times;
measuring, by an optical measurement device, a change in brain activity of the subject when the load is applied in the applying the load the plurality of times, and acquiring measurement data, the change in brain activity of the subject comprises a plurality of change measurements; and
determining, by a processor, a degree of cognitive function of the subject based on comparing the plurality of change measurements with one another such that a significant difference between a first change measurement and a second change measurement indicates that the subject is a non-demented person and no significant difference between the first change measurement and the second change measurement indicates that the subject has cognitive impairment; wherein an intensity of the sensory stimulus to be applied to the subject in the applying the load the plurality of times is increased each time the stimulus is applied regardless of a subject's response to any previously applied load when the change in brain activity of the subject is measured for determining the degree of cognitive function of the subject.

2. The cognitive function determination method according to claim 1, further comprising:

giving each of a plurality of types of sensory to the subject the plurality of times;

measuring the change in the brain activity of the subject when the sensory stimuli are each given in the giving each of the plurality of types of the sensory stimuli the plurality of times, and acquiring the measurement data of each of the plurality of types of the sensory stimuli; and determining the degree of the cognitive function of the subject based on a result obtained by combining the amount of change in the measurement data of each of the plurality of types of the sensory stimuli acquired when each of the plurality of types of the sensory stimuli is given.

3. The cognitive function determination method according to claim 1, wherein when the sensory stimulus is applied the plurality of times, the sensory stimulus to be applied to the subject is a persistent stimulus.

4. The cognitive function determination method according to claim 3, wherein the persistent stimulus is a stimulus given persistence by applying the sensory stimulus while an influence of a previous stimulus remains when the sensory stimulus is applied to the subject.

5. The cognitive function determination method according to claim 3, wherein the persistent stimulus is a cold stimulus.

6. The cognitive function determination method according to claim 1, wherein the sensory body is a hand of the subject; and the sensory stimulus is a contact stimulus.

7. The cognitive function determination method according to claim 1, wherein in the acquiring the measurement data, a measurement site is set within a range including any of F3, F4, P3, and P4 in accordance with International 10-20 system.

8. The cognitive function determination method according to claim 1, wherein the optical measurement device measures change in cerebral blood flow of the subject by near-infrared spectroscopy.

9. A cognitive function determination method comprising:

applying a load including tasks with different degrees of difficulty to a subject a plurality of times;

measuring, by an optical measurement device, a change in brain activity of the subject when the load is applied in the applying the load the plurality of times, and acquiring measurement data, the change in brain activity of the subject comprises a plurality of change measurements; and determining a degree of cognitive function of the subject based on comparing the plurality of change measurements with one another such that a significant difference between a first change measurement and a second change measurement indicates that the subject is a non-demented person and no significant difference between the first change measurement and the second change measurement indicates that the subject has cognitive impairment; wherein in the applying the load including the tasks with the different degrees of difficulty to the subject the plurality of times, when the change in brain activity of the subject is measured for determining the degree of cognitive function of the subject, the degrees of difficulty of the tasks are set such that a degree of difficulty of a second task given after a first task is higher than a degree of difficulty of the first task regardless of a subject's response to the first task.

10. The cognitive function determination method according to claim 9, wherein the tasks with the different degrees of difficulty are tasks related to at least one of calculation, a combination of memory and imagination, and spatial recognition; and the cognitive function determination method further comprises:

giving each of a plurality of types of the tasks with the different degrees of difficulty to the subject the plurality of times;

measuring the change in the brain activity of the subject when the tasks are each given in the giving each of the plurality of types of the tasks the plurality of times, and acquiring the measurement data of each of the plurality of types of the tasks; and determining the degree of the cognitive function of the subject based on a result obtained by combining the amount of change in the measurement data of each of the plurality of types of the tasks acquired when each of the plurality of types of the tasks with the different degrees of difficulty is given.

11. The cognitive function determination method according to claim 9, wherein the giving the tasks with the different degrees of difficulty the plurality of times includes repeatedly presenting, to the subject, tasks related to calculation with different degrees of difficulty.

12. The cognitive function determination method according to claim 9, wherein the giving the tasks with the different degrees of difficulty the plurality of times includes repeatedly presenting, to the subject, tasks in combination of memory with imagination with different degrees of difficulty.

13. The cognitive function determination method according to claim 9, wherein the giving the tasks with the different degrees of difficulty the plurality of times includes repeatedly presenting, to the subject, tasks related to spatial recognition with different degrees of difficulty.

14. The cognitive function determination method according to claim 9, wherein in the acquiring the measurement data, a measurement site is set within a range including any of F3, F4, P3, and P4 in accordance with International 10-20 system.

15. The cognitive function determination method according to claim 9, wherein the optical measurement device measures change in cerebral blood flow of the subject by near-infrared spectroscopy.

* * * * *